US005744324A

United States Patent [19]
Lester et al.

[11] Patent Number: 5,744,324
[45] Date of Patent: Apr. 28, 1998

[54] NUCLEIC ACIDS ENCODING POTASSIUM CHANNELS WHICH FORM INWARD RECTIFIER, G-PROTEIN ACTIVATED, MAMMALIAN, HETEROMULTIMERIC, POTASSIUM CHANNELS AND USES THEREOF

[75] Inventors: Henry A. Lester, South Pasadena; Norman Davidson, Sierra Madre; Paulo Kofuji, Pasadena, all of Calif.

[73] Assignee: California Institute of Technology, Pasadena, Calif.

[21] Appl. No.: 614,801

[22] Filed: Mar. 7, 1996

Related U.S. Application Data

[63] Continuation-in-part of Ser. No. 66,371, Mar. 21, 1993.
[51] Int. Cl.⁶ .......................... C12N 15/12; C12N 15/63; C12N 5/10; G01N 33/48
[52] U.S. Cl. .................. 435/69.1; 536/23.1; 536/23.5; 435/7.2; 435/325; 530/350
[58] Field of Search .................. 536/23.1, 23.5; 435/69.1, 240.2, 320.1, 7.2, 325, 375; 530/350

[56] References Cited

PUBLICATIONS

Wallace et al. (1987) Methods In Enzymology 152:432–442.
Sambrook, J., et al., "Synthetic Oligonucleotide Probes," *Molecular Cloning*, 2nd Ed. Cold Spring Harbor: New York, Chapter 11 pp. 11.1–11.60 (1989).
Dascal, N., et al., "Atrial G Protein–Activated K⁺ Channel: Expression Cloning and Molecular Properties," *PNAS, USA*, 90:10235–10239 (1993).
Dascal, N., et al., "Expression of an Atrial G–Protein–Activated Potassium Channel in Xenopus Oocytes," *PNAS, USA*, 90:6596–6600 (1993).
Hemmings, B.A., "α– and β–Forms of the 65 kDA Subunit of Protein Phosphatase 2A Have a Similar 39 Amino Acid Repeating Structure," *Biochem.*, 29:166–3173 (1990).
Ho, K., et al., "Cloning and Expression of an Inwardly Rectifying ATP–Regulated Potassium Channel," *Nature*, 362:31–38 (1993).
Kubo, Y., et al., "Primary Structure and Functional Expression of a Mouse Inward Rectifier Potassium Channel," *Nature*, 362:127–133 (1993).
Karschin, A., et al., "Heterologously Expressed Serotonin 1A Receptors Couple to Muscarinic K⁺ Channels in Heard," *PNAS, USA*, 88:5694–5698 (1991).
Adams, M.D., et al., "Sequence Identification of 2,375 Human Brain Genes," *Nature*, 355:632–634 (1992).
Lesage, F., et al., "Cloning Porvides Evidence for a Family of Inward Rectifier and G–Protein Coupled K⁺ Channels in the Brain," *FEBS. Lett.*, 35:37–42 (1994).
Sakmann, B., et al., "Acetylcholine Activation of Single Muscarinic K⁺ Channels in Isolated Pacemaker Cells of the Mammalian Hear," *Nature*, 303:250–253 (1983).
Yatani, A., et al., "Direct Activation of Mammalian Atrial Muscarinic Potassium Channels by GTP Regulatory Protein $G_k$," *Science*, 235:207–211 (1987).

Kubo, Y., et al., "Primary Structure and Functional Expression of a Rat G–Protein–coupled Mascarinic Potassium Channel," *Nature*, 364:802–806 (1993).
Alrich, R., "Advent of a New Family," *Nature*, 362:107–108 (1993).
Adams, R.L.P., et al., "Biochemistry of the Nucleic Acids," 9th Ed. London: Chapman and Hall, p. 174 (1981).
Krapivinsky, G., et al., "The G–Protein–Gated Atrial K+ Channel $I_{KACh}$ is a Heteromultimer of Two Inwardly Rectifying K⁺–Channel Proteins," *Nature*, 374:135–141 (1995).
Doupnik, C.A., "The Inward Rectifier Potassium Channel Family," *Current Opinion in Neurobiology*, 5:268–277 (1995).
Kofuji, P., "Evidence that Neuronal G–Protein–Gated Inwardly Rectifying K⁺ Channels are Activated by Gβγ Subunits and Funtion as Heteromultimers," *PNAS USA*, 92:6542–6546 (1995).
Brown, A.M. "Regulation of Heartbeat by G Protein––Coupled Ion Channels," *Am. J. Physiol.*, 259(6):H1621–H1628 (1990).
Kirsch, G.E. and A.M. Brown, "Trypsin Activation of Atrial Muscarinic K⁺ Channels," *Am. J. Pysiol.*, 26(1):h334–h338 (1989).
Duprat et al. (1995) Biochem. Biophys. Res. Comm. 212:657–663.
Lesage et al. (1995) J. Biol. Chem. 270: 28660–28667.
Kubo et al. (1993) Nature 364:802–806.

*Primary Examiner*—Stephen Walsh
*Assistant Examiner*—Michael D. Pak
*Attorney, Agent, or Firm*—Flehr Hohbach Test Albritton & Herbert LLP

[57] ABSTRACT

Compositions and methods are provided for producing functional mammalian inward rectifier, G-protein activated potassium channels (Kir3.0 channels). A channel is a multimeric protein comprising one or more Kir3.0 polypeptides, e.g. Kir3.1, Kir3.2, etc., where the polypeptides may be from the same or different species. The functional channel has the distinctive features of an anomalous rectifier, in that it conducts inward but not outward K⁺ current; it is blocked by low concentrations of extracellular $Cs^+$ or $Ba^{2+}$; and the conductance of the channel does not depend solely on voltage, but on $(E—E_K)$. The ability of the channel to conduct inward K⁺ current is modulated by G-proteins, particularly G-proteins of the $G_i/G_o$ family. A number of mammalian cell surface receptors activate G-proteins as a consequence of specific ligand binding. The signal transduction from receptor to Kir3.0 channel is therefore coupled through G-protein intermediates.

The functional Kir3.0 channels are useful in drug screening assays directed to modulation of cellular electrophysiology. Nucleic acids encoding Kir3.0 polypeptides are useful for expression of the gene product, and for identification of homologous genes from other species, as well as other members of the same family of proteins. Expression of the nucleic acids in a heterologous cell, e.g. Xenopus oocyte, confers the ability to cause a change in potassium flow in response to G-protein activation.

19 Claims, 6 Drawing Sheets

ND 96

HIGH K⁺

HIGH K⁺ + 5HT

NET $I_{5HT}$
600 nA
40ms

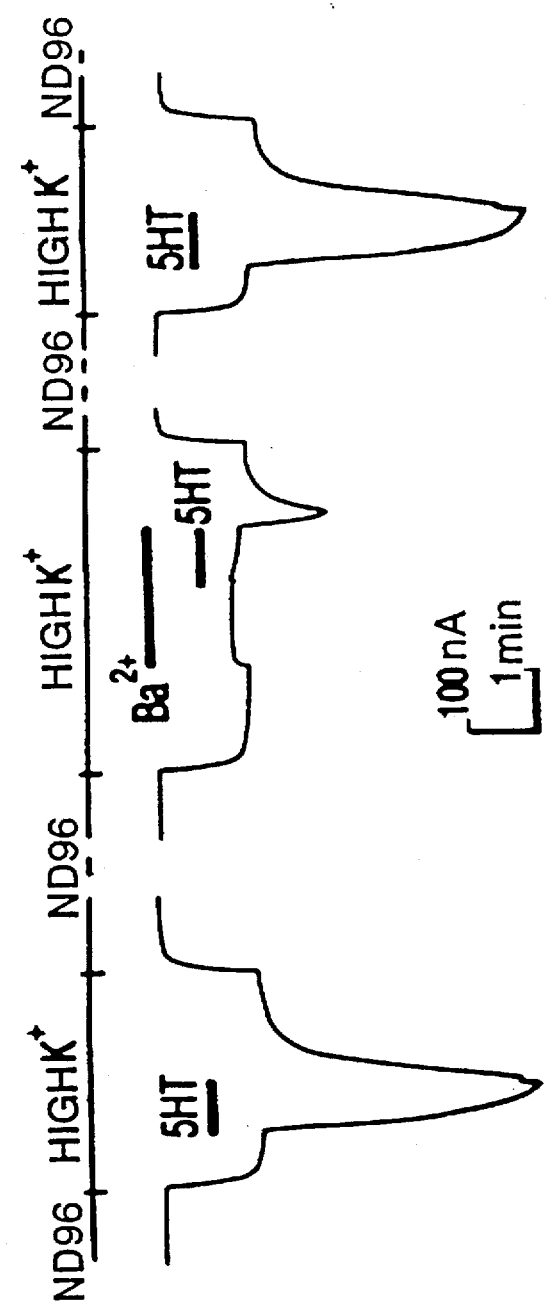

NUCLEIC ACIDS ENCODING POTASSIUM CHANNELS WHICH FORM INWARD RECTIFIER, G-PROTEIN ACTIVATED, MAMMALIAN, HETEROMULTIMERIC, POTASSIUM CHANNELS AND USES THEREOF

This application is a continuation-in-part of U.S. patent application Ser. No. 08/066,371, filed Mar. 21, 1993.

The invention disclosed herein was made with U.S. Government support under USPHS grants GM29836 and MH49176. The U.S. government has certain rights in this invention.

INTRODUCTION

BACKGROUND

The regulation of heart rate in response to stress, activity, and other stimuli is essential for mammalian survival. While each independent head muscle has an inherent faculty for independent excitation, the heartbeat is initiated in a specialized group of muscle cells in the sinoatrial node of the heart, which form the pacemaker. The heart is also innervated by nerves that regulate the beat. When these nerves are active, they liberate chemicals such as noradrenaline or acetylcholine from their terminals, and these neurotransmitters affect the cardiac muscles directly. The pacemaker is inhibited by acetylcholine and excited by noradrenaline.

The release of acetylcholine (ACh) opens a $K^+$ channel in the atrium, slowing the rate of depolarization that leads to initiation of the action potential. This effect is mediated through a G-protein signal transduction pathway, involving a pertussis toxin-sensitive, heterotrimeric G-protein, $G_k$, probably belonging to the $G_i/G_o$ family. Activation of the $K^+$ channel by $G_k$ does not require cytoplasmic intermediates, suggesting direct coupling of one or more G-protein subunits to the channel. However, a long-standing controversy exists as to which subunit couples to the channel. Both purified $\beta\gamma$ subunit complex and $\alpha$ subunits of the $G_i/G_o$ family activate the channel in cell free, inside-out patches of atrial myocytes. Activation by the $\alpha$ subunits occurs at lower concentrations than that by $\beta\gamma$, but seems to be less efficient. The relative physiological importance of each pathway, as well as of possible involvement of the arachidonic acid pathway, is unclear.

A similar $K^+$ channel is activated in the atrium by adenosine, ATP and epinephrine, probably also via a G-protein pathway. Furthermore, in nerve cells various 7-helix receptors, such as serotonin 5HT1A, $\alpha$-opioid, $GABA_B$ and somatostatin couple to similar $K^+$ channels, probably through direct activation by G-proteins. The similarity of the channels and signaling pathways in atrium and nerve cells is also shown by the coupling of a neuronal 5HT1A receptor (5HT1A-R) to the atrial channel, through transient expression in myocytes.

By electrophysiological and pharmacological criteria, these $K^+$ channels belongs to a family of inward rectifiers that conduct $K^+$ much better in the inward than the outward direction, are blocked by extracellular $Cs^+$ and $Ba^{2+}$, and are believed to possess a single-file pore with several permeant and blocking ion binding sites. Recently, the primary structures of two mammalian inward rectifier channels have been elucidated by cDNA cloning: an ATP-regulated $K^+$ channel from kidney, and an inward rectifier from a macrophage cell line. Both appear to belong to a new superfamily of $K^+$ channels, with only two transmembrane domains per subunit and a pore region homologous to that of $K^+$, $Ca^{2+}$ and $Na^+$ voltage-dependent channels.

G-protein regulated $K^+$ channels are important for the regulation of heart and nerve function. Determination of their molecular structure and regulation is therefore of great interest. Cloning of the channel protein genes and expression in a heterologous system would allow a molecular approach to investigation and manipulation of these regulatory pathways.

RELEVANT LITERATURE

The activation of atrial $K^+$ channels by G-proteins is reviewed in Kurachi et al. (1992) Prog. Neurobiol. 39:229–246; and Brown and Birnbaumer (1990) A. Rev. Physiol. 52:197–213. Logothetis et al. (1987) Nature 325:321–326 and Kurachi et al. (1989) Pflugers Arch. 413:325–327 provide evidence for activation by the $\beta\gamma$ subunits. Codina et al. (1987) Science 236:442–445 show activation by the $\alpha$-subunit. Karschin et al. (1991) P.N.A.S. 88:5694–5698 demonstrates the coupling of a neuronal receptor to the atrial $K^+$ channel.

Physiological characterization of the atrial $K^+$ channels is reviewed by Hille, B. (1992) Ionic Channels of Excitable Membranes, 2nd edition (Sinauer, Sunderland, Mass.). The role of $Mg^{2+}$ in blocking $K^+$ efflux is discussed in Horie and Irisawa (1987) Am. J. Physiol. 253: H210–H214.

The sequence characterization of a mammalian inward rectifier $K^+$ channel is disclosed in Ho et al. (1993) Nature 362:31–38; and Kubo et al. (1993) Nature 362:127–132. A brief review of these inward rectifying $K^+$ channels may be found in Aldrich (1993) Nature 362:107–108.

SUMMARY OF THE INVENTION

Compositions and methods are provided for producing functional mammalian inward rectifier, G-protein activated potassium channels (Kir3.0 channels). The functional channels comprise one or more polypeptides from the Kir3.0 subfamily of inward rectifier potassium channels. The effect that G-protein subunits exert on channel activity is determined by the specific composition of polypeptides in the channel. The functional Kir3.0 channels are useful in drug screening assays directed to modulation of cellular electrophysiology. Nucleic acids encoding Kir3.0 polypeptides are useful for expression of the gene product, and for identification of homologous genes from other species, as well as other members of the same family of proteins.

Figure 1A:
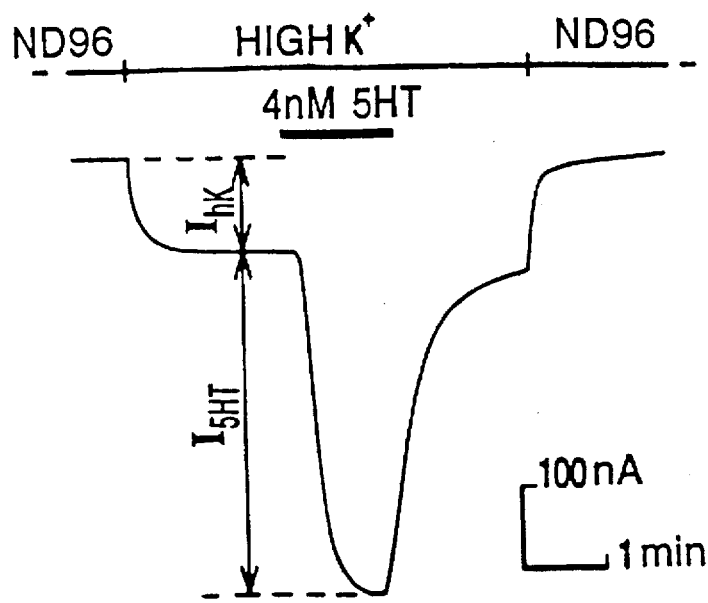
FIG. 1 shows inward currents evoked by high $K^+$, 5HT and ACh in RNA-injected oocytes. (A) $I_{hk}$ and $I_{5HT}$ in an oocyte injected with atrial RNA+5HT1A-R RNA. Holding potential in this and all following figures was −80 mV. (B) Inward currents evoked by ACh (AcCHo) and 5HT in a single oocyte in hK solution. (C) The dependence of $I_{5HT}$ amplitude on 5HT concentration in oocytes of one frog. In each oocyte, the response to one 5HT concentration was tested. Data represent mean±SEM in 4–6 cells at each concentration.

FIG. 3. Ba$^{2+}$ block of $I_{hK}$ and $I_{5HT}$ (A–C), records taken from the same oocyte at 10 min intervals. Between the records, the cell was bathed in ND96. 5HT concentration was 4 nM. Note that in (B) 300 μM Ba$^{2+}$ reduces $I_{hK}$ and almost completely blocks $I_{5HT}$. Ba$^{2+}$ and 5HT were washed out simultaneously, and this resulted in an inward current "tail". (D) dose dependence of Ba$^{2+}$ inhibition of $I_{hK}$ in native oocytes ○, $I_{hK}$ in RNA-injected oocytes ●, $I_{5HT}$ in RNA-injected oocytes ▽. Data are mean±SEM, n=3 to 7 for each point.

FIG. 4. $I_{5HT}$ is mediated by activation of a G-protein. (A) The effect of PTX treatment (500 ng/ml, 20–26 h) on $I_{hK}$ and $I_{5HT}$. The cells were injected with 120 ng/oocyte total atrial RNA, 11 ng/oocyte 5HT1A-R RNA, and, where indicated, with 11 ng/oocyte $G_{i2}\alpha$ RNA. (B) GDP-β-S injection inhibits $I_{5HT}$ but not $I_{hK}$ in an oocyte injected with atrial +5HT1A-R RNAs. 5HT concentration was 0.4 μM. A small outward current deflection (denoted by ★) upon washout of 5HT was caused by an inadvertent perfusion of ND96 for a few seconds.

DATABASE REFERENCES AND NOMENCLATURE FOR SEQUENCES

Systematic nomenclature for the family of inward rectifying postassium channel proteins has been proposed by Doupnik et al. (1995) *Curr. Opin. Neu8;* 5:268–277. This family is characterized by the presence of only two transmembrane domains per subunit, and a pore region homologous to that of K$^+$, Ca$^{2+}$ and Na$^+$ voltage-dependent channels. As suggested by Doupnik et al, the G-protein regulated members of this family are grouped into the Kir3 subfamily, where "Kir3.0" designates the subfamily of genes and polypeptides, and Kir3.1, 3.2, etc. refer to the specific subfamily members. Other subfamilies include the ATP regulated channels predominantly expressed in the kidney (Kir. 0 subfamily), and the constitutively active, steep inward rectifying Kir2.0 subfamily.

"GIRK1/KGA" and "KGB" are renamed as Kir3.1. The Genbank accession numbers for these sequences, from different species, are L25264; U01071; U01141; and D45022.

"GIRK2" is renamed as Kir3.2. The Genbank accession numbers for these sequences, from different species, are U011860 and U24660. "GIRK3" is renamed as Kir3.3. The Genbank accession number for this sequence is U11860. "GIRK4", "rcKATP/CIR", "hcKATP" is renamed Kir3.4. The Genbank accession numbers for these sequences, from different species, are X83584; L35771; X83582; and L47208.

A large number of heterotrimeric G-proteins have been characterized. A review of the family and database accession numbers may be found in Watson and Arkinstall (1994) *The G-Protein Linked Receptor FactsBook*, Academic Press, Inc., San Diego, Calif., pp.296–355.

DETAILED DESCRIPTION OF THE INVENTION

Functional mammalian inward rectifier, G-protein activated potassium channels (Kir3.0 channels) are produced by expression of Kir3.0 genes. The multimeric channels vary in their response to G-protein activation, depending on the specific combination of Kir3.0 polypeptides. Drug screening assays directed to modulation of cellular electrophysiology are performed with isolated channels, membrane patches comprising channels, intact cells expressing heterologous channels, etc. Nucleic acids encoding Kir3.0 polypeptides are useful for expression of the gene product, and for identification of homologous genes from other species, as well as other members of the same family of proteins.

As used herein, the term "Kir3.0 channel" designates a functional multimeric protein that comprises one or more Kir3.0 polypeptides, preferably at least two different Kir3.0 polypeptides, e.g. Kir3.1, Kir3.2, Kir3.3, etc., where the polypeptides may be from the same or different species. The functional channel has the distinctive features of an inward rectifier, in that it conducts inward but not outward K$^+$ current; it is blocked by low concentrations of extracellular Cs$^+$ or Ba2+; and the conductance of the channel does not depend solely on voltage, but on (E—$E_K$). Characteristic of the Kir3.0 family, the ability of the channel to conduct K$^+$ current is modulated by G-proteins, particularly G-proteins of the $G_i/G_o$ family. It has been found that such modulation may be mediated directly by the G-protein βγ subunit. It will be understood by one of skill in the art that a number of mammalian cell surface receptors activate G-proteins as a consequence of specific ligand binding. The signal transduction from receptor to Kir3.0 channel can therefore be coupled through G-protein intermediates.

The specific combination of Kir3.0 polypeptides in the channel will determine the properties of the channel. As an example, it has been observed that a channel comprised of Kir3.1 and Kir3.2 polypeptides, or of Kir3.1 and Kir3.3 polypeptides, demonstrates a significant enhancement of the G-protein evoked currents. In contrast, a channel comprised of Kir3.2 and Kir3.3 polypeptides shows a decrease in G-protein evoked currents.

As used herein, the term Kir3.0 polypeptide is used to designate a single polypeptide that is capable of associating with other Kir3.0 polypeptides to form a functional Kir3.0 channel as defined above. When a nucleic acid encoding a Kir3.0 polypeptide is introduced into a cell, particularly a Xenopus oocyte, and expressed, it confers a change in the electrophysiology of the cell, such that the cell has an altered ability to conduct K$^+$ current, particularly in response to G-protein activation. Genes encoding Kir3.0 polypeptides can be identified in such a system based on the expression of a single gene, or a combination of genes. The ability of Kir3.0 polypeptides to associate and form multimeric channels in a cell provides a means of identifying genes encoding novel Kir3.0 polypeptides, where a candidate gene may be introduced into a cell comprising a known Kir3.0 gene. A change in the electrophysiology of the cell, as described above, is indicative that the candidate gene encodes a Kir3.0 polypeptide able to partake in multimeric channel formation.

Kir3.0 polypeptides may also be characterized by sequence similarity to known members of the Kir3.0 family. SEQ ID NO:2 describes an exemplary Kir3.1 polypeptide, of rat origin. Within a species, various members of the Kir3.0 gene family will usually have at least about 50% amino acid sequence identity, more usually at least about 60%, and may be as high as 70 to 80%. Between mammalian species, the homologous Kir3.0 polypeptides, e.g. human and rat Kir3.1, etc., have a high degree of similarity, usually at least about 75% amino acid sequence identity, more usually at least about 85% sequence identity, and may be as high as 90% sequence identity, particularly in the conserved transmembrane and pore forming regions.

For convenience in experimental manipulation and drug screening assays, the Kir3.0 channel may be assembled in an expression host cell. As used herein, art expression host cell is a cell, preferably a eukaryotic cell having substantially no endogenous Kir3.0 channels. The expression host will have introduced into it one or more different exogenous nucleic acid(s) encoding one or more Kir3.0 polypeptides, preferable at least two polypeptides. Such exogenous nucleic acids will be capable of constitutive or inducible expression of the Kir3.0 nucleic acid(s) in the host cell. Where two or more polypeptides are present, the genes encoding Kir3.0 polypeptides may be on a single vector or DNA molecule, or may be present on separate molecules. The expression of the exogenous nucleic acid causes an altered ability to conduct $K^+$ current in the expression host cell, particularly in response to G-protein activation. For example, nucleic acids encoding one or more mammalian Kir3.0 polypeptides can be inserted into a host cell, e.g. Xenopus oocyte; yeast; mammalian immortalized cell line or primary cell culture; plant cell; etc. by transfection, injection, transduction, etc. Expression of the nucleic acid produces Kir3.0 polypeptides, which will assemble into a channel in the membrane of the host cell. It has been found in some cases that the heterologous Kir3.0 polypeptide will assemble with polypeptides of the heterologous host cell to form a hybrid channel. Cell surface receptors, such as muscarinic receptors, serotonin receptors, etc., and G-proteins may additionally be introduced into the heterologous host cell. A functional heterologous channel will regulate inward $K^+$ current in response to the presence of exogenous or endogenous activated G-proteins.

The Kir3.0 channels in homologous or heterologous cells are useful in the study of cell electrophysiology, including but not limited to neural and cardiac cells, particularly G protein linked responses, such as those coupled to acetylcholine and serotonin receptor binding. Of particular interest are in vitro drug screening assays. Screening assays are provided to identify drug candidates that specifically alter Kir3.0 channel activity either directly or indirectly by modulating receptors, G-proteins, channels or the interactions among these elements. Novel binding agents include specific antibodies, natural or non-natural binding agents identified in screens of chemical libraries, analogs of acetylcholine, G proteins, etc. Areas of investigation include the development of cardiovascular, neurologic endocrine and gastrointestinal treatments.

Nucleic acid molecules are provided that encode individual polypeptides capable of forming a Kir3.0 channel. The subject polypeptide may be any one of Kir3.1 (for purposes of continuity referred to hereafter as Kir3.1/KGA), Kir3.2, Kir3.3, Kir3.4, etc. The origin of the nucleic acid may be any mammalian species, e.g. human, murine, primate, bovine, equine, canine, feline, ovine, porcine, etc.

"Kir3.0 genes" shall be intended to mean the nucleotide sequences encoding specific Kir3.0 polypeptides, as well as adjacent 5' and 3° non-coding nucleotide sequences involved in the regulation of expression of the protein encoded by the genes, and will include up to about the length of the mature mRNA. Also included is the corresponding genomic sequence, and may include up to 1 kb of flanking genomic DNA at either the 5' or 3' end of the coding region. These non-coding sequences include termination sequences, introns, regulatory protein binding sequences, translational regulatory sequences, and the like.

The nucleic acid compositions of the subject invention encode all or a part of the subject Kir3.0 polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, more usually at least 18 nt. Preferably fragments will encode a functional epitope or domain. The sequence providing for a functional epitope can be determined by expression of the sequence, and assaying for reactivity of the expression product with specific antibodies by conventional immunoassay, or by assaying for the ability of the fragment to create a polypeptide capable of assembling into a functional Kir3.0 channel.

The DNA sequences may be obtained in substantial purity, and will be obtained as a sequence other than a sequence of an intact chromosome. Usually, the DNA will be obtained substantially free of other nucleic acid compounds which do not include a Kir3.0 sequence or fragment thereof, generally being at least about 50%, usually at least about 90% pure and are typically "recombinant", i.e. flanked by one or more nucleotides with which they are not normally associated with on a natural chromosome.

The subject nucleic acids may be used in a variety of ways. They may be used as probes for identifying other Kir3.0 genes. Homologous sequences and related members of the Kir3.0 gene family are those with substantial sequence similarity to the subject sequences, as previously described. Algorithims for sequence analysis are known in the art, and include BLAST, described in Altschul et al (1990) *J Mol Biol* 215:403–10; ADVANCE and ADAM, described in Torelli and Robotti (1994) *Comput Appl Biosci* 10:3–5; and FASTA, described in Pearson and Lipman (1988) *P.N.A.S.* 85:2444–8.

Such homologous or related nucleic acid sequences are detected by hybridization under low stringency conditions, for example, at 50° C. and 10×SSC (0.9M saline/0.09M sodium citrate) and remain bound when subject to washing at 55° C. with 1×SSC. The high degree of similarity between Kir3.0 homologs allows the use of relatively stringent hybridization conditions, as known in the art. For example, see Sambrook et al. *Molecular Cloning* (Cold Spring Harbor, N.Y., 1989). By using probes, particularly labeled probes of DNA sequences, one may be able to isolate homologous genes, which may be then used for identifying members of the Kir3.0 family in other species. By probes is intended a single stranded oligonucleotide of at least about 12 nt in length, more usually at least about 15 nt, and preferably at least about 18 nt, characterized by the ability to hybridize under low stringency conditions to Kir3.0 genes. The term "unique" as used herein defines a nucleic acid molecule that does not contain known genomic repeated sequences, including but not limited to Alu sequences.

Various methods are known in the art for identification of nucleic acids having sequence similarity, based on the ability of single stranded nucleic acids, e.g. DNA to form a double stranded complex. A sample may be screened for the presence of nucleic acids capable of forming double stranded complexes with a Kir3.0 probe, particularly under low stringency conditions. "Sample" as used herein includes but is not limited to genomic libraries, cDNA libraries, nucleic acid molecule extracts from tissue, or nucleic acid molecule extracts from cell culture. After complex formation, the other nucleic acid molecule is isolated by methods known in the art. Methods include the polymerase chain reaction (PCR) or reverse transcriptase PCR (RT-PCR), where two probes from the subject nucleic acids sequence are used to amplify a region of the sample DNA or cDNA. PCR may also be performed with a single Kir3.0 probe, and a second oligonucleotide complementary to a known genomic repeat sequence. Alternatively, northern or southern blots are useful in identifying bands, colonies, plaques, etc. comprising nucleic acids capable of hybridizing to a Kir3.0 probe. Generally the Kir3.0 probe will be labeled with a detectable marker, e.g. $^{32}P$, $^{35}S$, biotin, FITC, etc. when used in a northern or southern blot.

The subject nucleic acids may also be used to identify the expression of Kir3.0 genes in a biological specimen. The manner in which one probes cells for the presence of particular nucleotide sequences, particularly as genomic DNA, is well-established in the literature and does not require elaboration here. Conveniently, a biological specimen is used as a source of mRNA. The mRNA may be amplified by polymerase chain reaction using primers specific for the subject DNA sequences. Alternatively, the mRNA sample is separated on gel electrophoresis and then probed using Northern blotting with a fragment of the subject DNA as a probe. Other techniques may also find use. Detection of mRNA having the subject sequence is indicative of Kir3.0 expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence; or the like. Modifications may include replacing oxygen of the phosphate esters with sulfur or nitrogen, replacing the phosphate with carboxamide, phosphoramide, etc.

The DNA sequence may encode amino acid sequences that differ from the native sequence of a Kir3.0 polypeptide, but that do not produce functional changes in the Kir3.0 polypeptide. The sequence may encode polypeptide analogs, fragments or derivatives of substantially similar polypeptides that differ from the naturally-occurring forms in terms of the identity of location of one or more amino acid residues (deletion analogs containing less than all of the residues specified for the protein, substitution analogs wherein one or more residues are replaced by other residues and addition analog wherein one or more amino acid residues is added to a terminal or medial portion of the polypeptides) and which share some or all properties of naturally-occurring forms. These sequences include the incorporation of preferred codons for expression in non-mammalian host cells; the provision of sites for cleavage by restriction endonuclease enzymes; the addition of promoters operatively linked to enhance RNA transcription; and the provision of additional initial, terminal or intermediate DNA sequences that facilitate construction of readily expressed vectors.

For expression, the DNA sequences may be inserted into an appropriate expression vector, where the native transcriptional initiation region may be employed or an exogenous transcriptional initiation region, i.e. a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts, where the expression hosts may involve prokaryotes or eukaryotes, particularly E. coil; B. subtilis; yeast cells; mammalian cells; e.g. Cos cells, HeLa cells, L(tk-), primary cultures; insect cells; Xenopus laevis oocytes; and the like. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g. β-galactosidase, etc.

Expression vectors may also be used to produce mRNA encoding a Kir3.0 polypeptide. The mRNA may be isolated, and used for synthesis of the polypeptide by injecting the RNA molecules into Xenopus oocytes and culturing the oocytes under conditions that are well known to an ordinary artisan.

The subject nucleic acids are used to identify nucleic acids encoding receptors and G-proteins that modulate the activity of Kir3.0 channels by activating or deactivating the channel. As previously described, such methods may also be used to identify genes encoding novel Kir3.0 polypeptides as well. A candidate nucleic acid or library of nucleic acids may be introduced into an expression host cell comprising a Kir3.0 channel, and the host cell screened for a change in the Kir3.0 channel activity. The candidate nucleic acid or library of nucleic acids may be selected from a variety of sources, including cDNA expression constructs operable in the host cell or mRNA transcribed in vivo or in vitro and subsequently introduced into the host cells. Pools of different nucleic acids may be tested, where positive pools are then used to generate smaller pools or individual clones. Nucleic acids that give a positive signal for modulation of Kir3.0 channel activity are then isolated and characterized as to the nucleic acid sequence and structure. The change in channel activity may be the result of expression of the candidate nucleic acid directly, or a known activating agent may be added to the cells to effect a change in channel activity.

A candidate nucleic acid encoding a putative receptor or G protein that interacts with tile subject channels may be tested for its ability to modulate Kir3.0 channel activity. The candidate nucleic acid is introduced into an expression host in conjunction with a Kir3.0 expression construct of one or more Kir3.0 polypeptides, preferably at least two polypeptides. The expression host is contacted with a known G-protein associated receptor activator, where an increase in Kir3.0 channel conductance indicates activation of the channel, and a decrease in conductance indicated inhibition of the channel.

Expression cassettes may be prepared comprising a transcription initiation region, which may be constitutive or inducible, the gene encoding the subject methyltransferase or fragment thereof, and a transcriptional termination region. Of particular interest is the use of sequences which allow for the expression of functional epitopes or domains, usually at least about 24 nucleotides in length, more usually at least about 48 nucleotides in length, and up to the complete open reading frame of the gene. After introduction of the DNA, the cells containing the construct may be selected by means of a selectable marker, the cells expanded and then used for expression.

The expression cassettes may be introduced into a variety of vectors, where the vectors will normally be characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence will be provided for the replication of the plasmid, which may be a low- or high-copy plasmid. A wide variety of markers are available for selection, particularly those which protect against toxins, more particularly against antibiotics. The particular marker that is chosen will be selected in accordance with the nature of the host, where in some cases, complementation may be employed with auxotrophic hosts, e.g. bacteria, yeast. Introduction of the DNA construct may be by any convenient means, e.g. conjugation, calcium-precipitated DNA, electroporation, fusion, transfection, infection with viral vectors, etc.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to 100% pure. By pure is intended free of other proteins, as well as cellular debris.

The polypeptide may be used for the production of antibodies. Antibodies may be prepared in accordance with conventional ways, where the expressed polypeptide or protein is used as an immunogen, by itself or conjugated to known immunogenic carriers, e.g. KLH, BSA, etc. Various adjuvants may be employed, as appropriate. For monoclonal antibodies, after one or more booster injections, the spleen of the immunized animal is isolated, the splenocytes immortalized, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor laboratories, Cold Spring Harbor, N.Y., 1988. The antibodies may find use in diagnostic assays for detection of the presence of Kir3.0 channels in patient samples.

By providing for the production of large amounts of Kir3.0 polypeptides and channels, one can identify ligands or substrates which bind to, or modulate the action of Kir3.0 channels. The subject Kir3.0 channels, polypeptides or functional domains thereof are used to screen for agonists or antagonists that modulate the $K^+$ channel activity, by increasing or decreasing the evoked $K^+$ current. In this way, drugs may be identified that can alter the electrophysiology of cells comprising Kir3.0 channels, including atrial, neural, vascular smooth muscle, endothelial, pancreatic and other cells. Of particular interest are screening assays for agents that have a low toxicity for human cells. A wide variety of assays may be used for this purpose, including whole cell or single channel current quantitation in response to stimulus, patch clamping, labeled in vitro protein-protein binding assays, electrophoretic mobility shift assays, immunoassays for protein binding, and the like.

In a preferred embodiment, a whole cell or single channel current will be quantitated in the presence of a candidate pharmacological agent. The assay will include contacting a cell into which has been introduced a functional Kir3.0 channel with a candidate pharmacological agent, and detecting any change in channel conductance. An increase in inward $K^+$ channel conductance indicates channel activation, while a decrease indicates that the agent is a channel inhibitor.

The term "agent" as used herein describes any molecule, protein, or pharmaceutical with the capability of directly or indirectly altering ion channel conductance by affecting second messenger systems, receptors, G-proteins, interactions among the elements, or the ion channel directly. Agents include but are not limited to serotonin, neurotropin, enkephalins, dopamine, arachidonic acid, cholera toxin, and pertussis toxin. Generally a plurality of assay mixtures are run in parallel with different agent concentrations to obtain a differential response to the various concentrations. Typically, one of these concentrations serves as a negative control, i.e. at zero concentration or below the level of detection.

The term "activators" as used herein defines any agent which activates a Kir3.0 channel, G-protein associated receptor or G-protein. The term "activates" as used herein is applied to both G-protein associated receptors and ion channel conductance and in terms of G-protein associated receptors defines the state of the receptor wherein it initiates release of a G-protein subunit which in turn initiates a cellular response. In terms of the ion channel conductance "activates" defines the state of the channel wherein the channel increases conductance. The term "deactivates" as used herein defines the state of the channel wherein the channel is initiated to decrease conductance or is incapable of conductance under conditions when the channel normally conducts ions across a membrane. The term "agonist" as used herein defines an agent that initiates activation of ion channel conductance or initiates activation of a second messenger system. The term "antagonist" as used herein defines an agent that initiates deactivation of ion channel conductance or initiates deactivation of a second messenger system.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon, heterocyclic or carbocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Various techniques for performing screening assays are known in the art. For example, a screening assay may utilize one or more molecules conjugated to a label, where the label can directly or indirectly provide a detectable signal. Various labels include radioisotopes, fluorescers, chemiluminescers, enzymes, specific binding molecules, particles, e.g. magnetic particles, and the like. A mixture of the components are added to the assay sample, and the binding of candidate agents to the subject channels, receptors or G proteins is detected. Alternatively, a host cell expressing a Kir3.0 channel is combined with a candidate agent under conditions that induce a change in $K^+$ current.

When an agent is identified that has a desired pharmacological activity, it may be used for prophylactic, therapeutic or experimental purposes. Such agents find use in investigating the interactions of inward $K^+$ channels with surface membrane receptors, G-proteins and second messenger systems. For therapeutic use, the agent may be administered in a physiologically acceptable carrier to a host. The agents may be administered in a variety of ways, orally, parenterally e.g. subcutaneously, intraperitoneally, intravascularly, intralingually, topically, etc. Depending upon the manner of introduction, the compounds may be formulated in a variety of ways, where the concentration of therapeutically active compound in the formulation may vary from about 0.1–100 wt.%.

For convenience, a kit may be provided having the components necessary to perform the subject screening assays. Such a kit may contain at least one expression vector comprising a Kir3.0 gene. Usually at least two Kir3.0 genes will be included, which may be on one vector or two vectors. The kit may further comprise agents for the detection of $K^+$ current change, and agents having a known positive or negative effect on activity of Kir3.0 channels or receptors associated therewith.

The following examples are offered by way of illustration and not by way of limitation.

EXPERIMENTAL

Isolation of a cDNA Encoding Kir3.1/KGA

A cDNA plasmid library was made from 19-day-old rat atrial mRNA. The library was linearized and amplified by polymerase chain reaction using primers complementary to sequences flanking the cDNA insert. cRNA was synthesized in vitro from the T7 promoter and microinjected into Xenopus laevis oocytes. Electrophysiological recordings identified an inward rectifier, G-protein activated, potassium channel.

Materials and Methods

Preparation of RNA and oocytes. Total RNA was extracted from atria and ventricles of 19–21 day old rats of both sexes using the procedure of Chomczinski and Sacchi (1987) *Anal. Biochem.* 162:156–159. Poly (A) RNA was separated on an oligo-dT cellulose column (type 3, Collaborative Biochemical Products). Ventricle poly(A) RNA was fractionated by centrifugation (18 h, 30,000 g, 4° C.) on a linear 5%–25% sucrose gradient. Xenopus laevis oocytes were prepared as previously described (Dascal & Lotan (1992) in *Methods in Molecular Biology*, v. 13: *Protocols in Molecular Neurobiology*, eds. Longstaff & Revest). and injected with either 50–120 ng/oocyte poly(A) RNA, 120–200 ng/oocyte total RNA, or 35 ng/oocyte fractionated poly(A) RNA. In most cases, 5HT1A-R RNA (5–20 ng/oocyte) was co-injected with atrial or ventricle RNA. Final volume of the injected RNA solution was 50 nl. The oocytes were incubated for 3–7 days in the NDE solution (ND96 (see below) containing 1.8 Mm $CaCl_2$ and supplemented with 2.5 Mm Na-pyruvate and 50 µg/ml gentamicin). Occasionally, either 2.5–5% heat-inactivated horse serum or 0.5 mM theophylline were added to the NDE solution. Incubation of oocytes in pertussis toxin (PTX; List Biochemicals) was done in NDE solution without the addition of pyruvate, serum or theophylline. cDNAs of 5HT1A receptor (Karschin et. al. (1991) *P.N.A.S.* 88:5694–5698) and $G_{i2}a$ (a gift from M. I. Simon, Caltech) in pBluescript were linearized, and RNA was synthesized in vitro as described (Dascal and Lotan, supra.).

Electrophysiological recordings were performed using the two electrode voltage clamp method with the Dagan 8500 amplifier (Dagan Instruments, Minneapolis) as described (Dascal et al. (1986) *Mol. Brain Res.* 1:201–209). The oocytes were usually kept in the ND96 solution: 96 mM NaCl/2 mM KCl/1 mM $MgCl_2$/1 mM $CACl_2$/5 mM Hepes, pH=7.5. Most measurements were done in the high $K^+$ solution (hK): 96 mM KCl/2 mM NaCl/1 mM $MgCl_2$/1 mM $CACl_2$/5 mM Hepes, pH=7.5. Solutions containing intermediate concentrations of $K^+$ were made by substituting $K^+$ for $Na^+$. Solution exchange and drug application were done by superfusing the cell placed in a 0.5 ml chamber. GDP-β-S (trilithium salt; Sigma) was injected by pressure (Dascal et al. supra.). Stimulation, data acquisition, and analysis were performed using pCLAMP software (Axon Instruments, Foster City, Calif.).

RESULTS

To express the KG channel, the oocytes were injected with atrial total or poly(A) RNA. In order to avoid the possibility that a low level of expression of the muscarinic receptor will make undetectable even a well-expressed KG channel, atrial RNA was usually supplemented with mRNA coding for the serotonin-5HT1A receptor (5HT1A-R); oocytes injected with this RNA mixture will be termed RNA-injected oocytes throughout the paper. When expressed in atrial myocytes, the 5HT1A-R efficiently coupled to the KG channel normally existing in these cells (Karschin et al. supra.), and it was expected to do so in the oocytes.

Four to 5 days after RNA injection addition of 10 µM ACh or 1–2 µM 5HT to the ND96 bath solution did not cause any significant change in membrane current. Therefore, the effects of ACh and 5HT were tested in a high potassium (hK) solution with 96 mM $K^+$ and 2 mM $Na^+$. In this solution, the $K^+$ equilibrium potential ($E_K$) is close to 0 mV, and this enables inward $K^+$ current flow through inwardly rectifying K channels at negative holding potentials (−80 mV was routinely used in this study).

Changing ND 96 to the hK solution was accompanied by the development of an inward current that reached a steady level within 0.5–1 min ($I_{hK}$; FIG. 1A). $I_{hK}$ was also observed in native (not injected with any RNA) oocytes, or in oocytes injected with 5HT1A-R RNA alone, but it was always larger in RNA-injected oocytes (P<0.001, two-tailed t-test; Table 1).

TABLE 1

| 2 µM. Injected RNA | $I_{hK}$ | $I_{5HT}$ |
| --- | --- | --- |
| None (native oocytes) | 72 ± 6 (34) | 0 (18) |
| 5HT1A-R | 54 ± 4 (11) | 0 (12) |
| Atrial + 5HT1A-R | 123 ± 8 (55) | 290 ± 43 (55) |

Figure 1B:
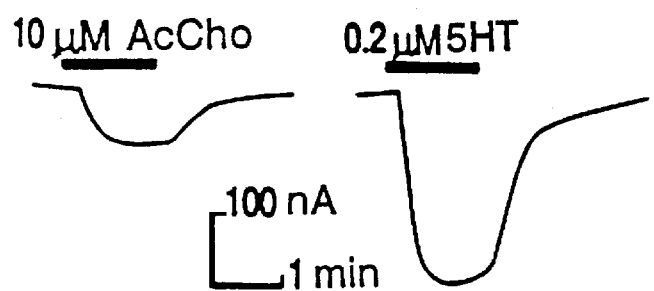

In RNA-injected oocytes, application of 5HT or ACh in hK solution induced an inward current ($I_{5HT}$) that subsided upon washout of the transmitter (FIG. 1A, B). The response to ACh was usually smaller than to 5HT when measured in the oocytes of the same frog (FIG. 1B). Thus, in oocytes of one frog $I_{5HT}$ was 1102±84 nA (n=6), whereas the ACh response was 382±45 nA(n=6). $I_{5HT}$ tended to decrease on repeated applications of 5HT, and this could be overcome by increasing the intervals between applications to 10 min or more, suggesting the presence of a desensitization process. $I_{5HT}$ and an increased (in comparison with native oocytes) $I_{hK}$ were also observed in oocytes injected with ventricle poly (A) RNA+5HT1A-R RNA, but the $I_{5HT}$ was about 20 times smaller than with atrial poly(A) RNA (not shown). 5HT had no effect in oocytes injected with atrial RNA without the 5HT1A-R RNA (n-4) or with 5HT1A-R RNA alone, or in native oocytes (Table 1).

Figure 1C:
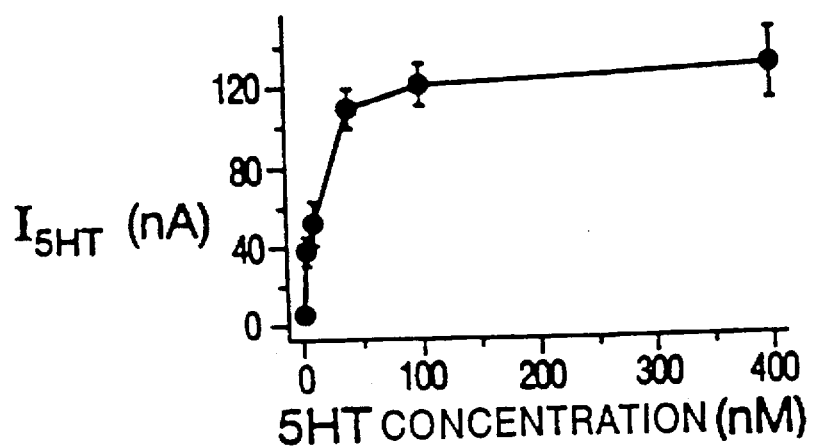

The 5HT dose-response curve showed saturation at about 100 nM and a half-maximal response at about 15 nM (FIG. 1C), which is characteristic of the 5HT1 receptor class (Hoyer & Schoeffer (1991) *J. Recept. Res.* 11:197–214). A similar current was evoked by a selective 5HT1A agonist, 8-OH DPAT (8-OH-2(D1-n-(propylamino)-tetralin ).

Figure 2A:
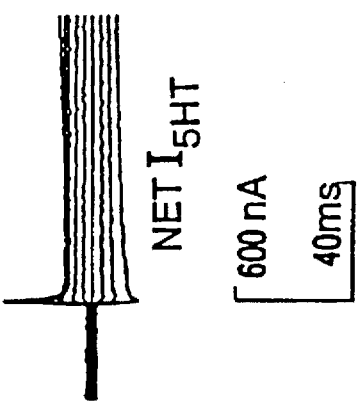
FIG. 2. $I_{hK}$ and $I_{5HT}$ are inwardly rectifying $K^+$ currents. (A–D) Currents evoked by voltage steps from the holding potential of −80 mV to voltages between −140 and 40 mV in 20 mV steps in ND96(A), hK (B), hK in the presence of 5HT (C). Net $I_{5HT}$(D) was obtained by digital subtraction of (B) from (C). (E) Current-voltage relations of the total membrane current in a representative oocyte in NG 96 (2 mM [$K_{out}$]; □), in 25 mM [$K^+_{out}$] ♦); in 75 mM [$K_{out}$] ○, and in hK (96 mM [$K_{out}$]; ▲). (F) Current-voltage relation of the net $I_{5HT}$ in the same oocyte as in (E) in 25 mM [$K_{out}$] ♦, 75 mM [$K_{out}$] ○, and 96 mM [$K_{out}$] ▲. (G) The dependence of the reversal potentials of total membrane current ♦ and of $I_{5HT}$ ● on [$K_{out}$]. The straight lines represent least square fits to data (mean±SEM, n=3 for each point).
Figure 2B:
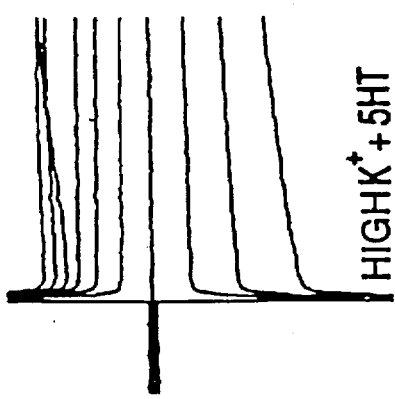
Figure 2C:
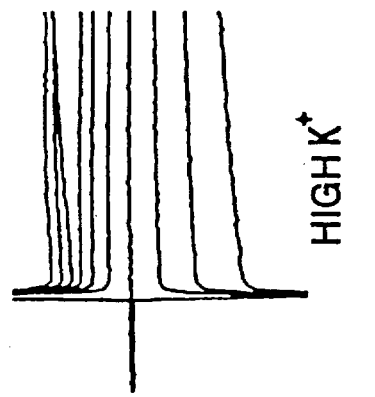
Figure 2D:
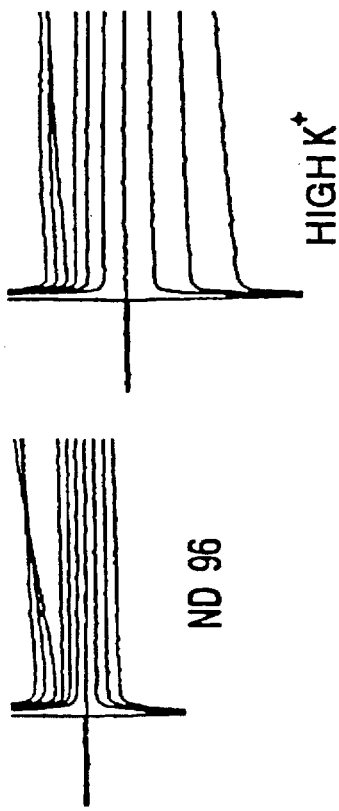
Figure 2E:
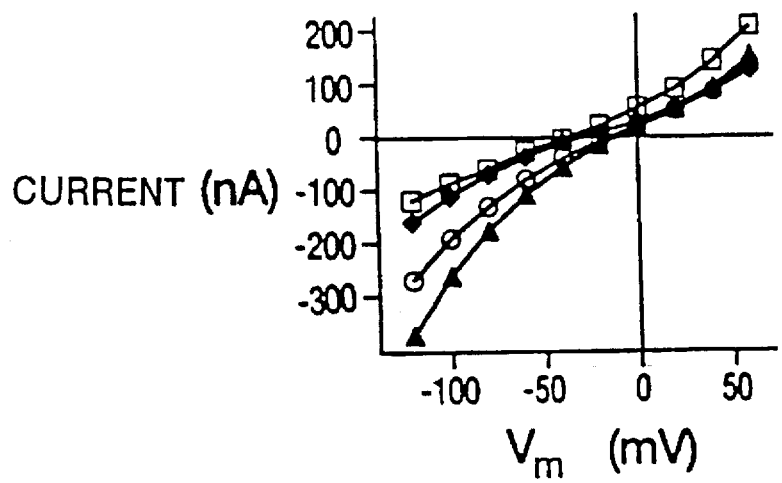
Figure 2F:
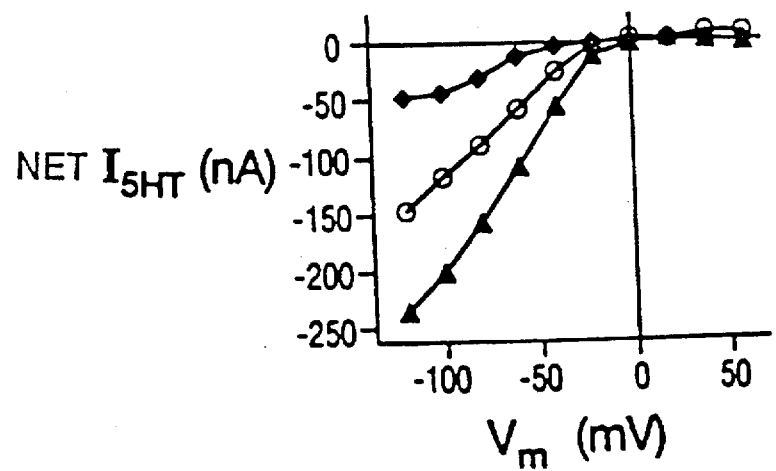
Figure 2G:
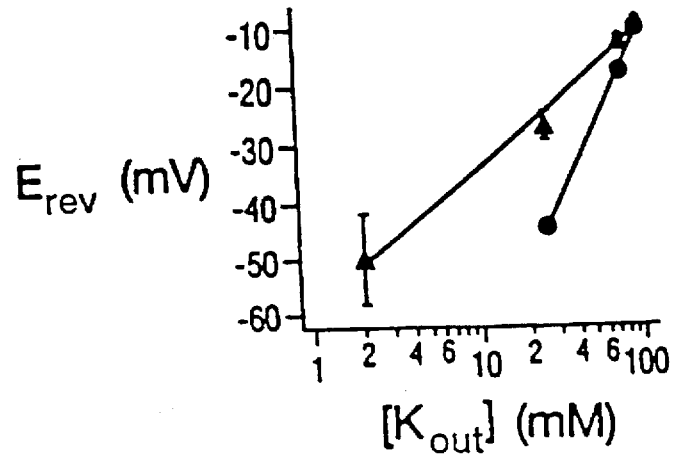

The current-voltage (I-V) characteristic of the oocyte membrane was studied by applying voltage steps from a holding potential of −80 mV. In normal ND96, in the range −140—20 mV, only voltage- and time-independent "leak" currents were observed (FIG. 2A), and the I-V curve was linear (FIG. 2E). Above −20 mV, a slowly developing outward current was observed (FIG. 2A–C); this is known to be due to opening of a Cl⁻ channel activated by $Ca^{2+}$ entry through voltage-dependent $Ca^{2+}$ channels (Barish (1983) *J. Physiol.* 342:309–325). The $Ca^{2+}$-activated Cl⁻ current was also seen in the hK solution; in addition, the total membrane current evoked by steps to −120 and up to −20 mV was larger than in ND96 (FIGS. 2B; 2E), whereas above 0 mV there was little or no change. This suggested that most or all of $I_{hK}$ elicited at −80 mV by the exchange of ND96 to hK solution was due to a $K^+$ current flowing through a constitutively active inward rectifier $K^+$ channel(s). This current showed some time-dependent inactivation at −140 mV (FIG. 2B) and at more negative potentials; this inactivation phenomenon was not studied further. In the presence of 5HT, the membrane currents between −140 and −20 mV were further increased (FIG. 2C). Net 5HT-evoked currents, obtained by digital subtraction of total membrane currents in the absence of 5HT from currents in its presence (FIG. 2D), showed clear inward rectification; the 5HT-activated channels conducted little or no current above $E_K$ at different external $K^+$ concentrations, $[K_{out}]$ (FIG. 2F). The extrapolated reversal potential of $I_{5HT}$ showed an almost perfect selectivity of the 5HT-activated channel to $K^+$, changing by about 58 mV per 10-fold change in $[K_{out}]$ (FIG. 2G). The reversal potential of the total membrane current in the absence of 5HT also depended on $[K_{out}]$ (FIG. 2E) but changed only by 24 mV per tenfold change in $[K_{out}]$ (FIG. 2G). This does not necessarily imply poor ion selectivity of the constitutively active inward rectifier, but may reflect the relatively high contribution of Cl⁻ and $Na^+$ to the resting membrane conductance (Dascal et al. (1984) *J. Physiol.* 352:551–574).

Figure 3D:
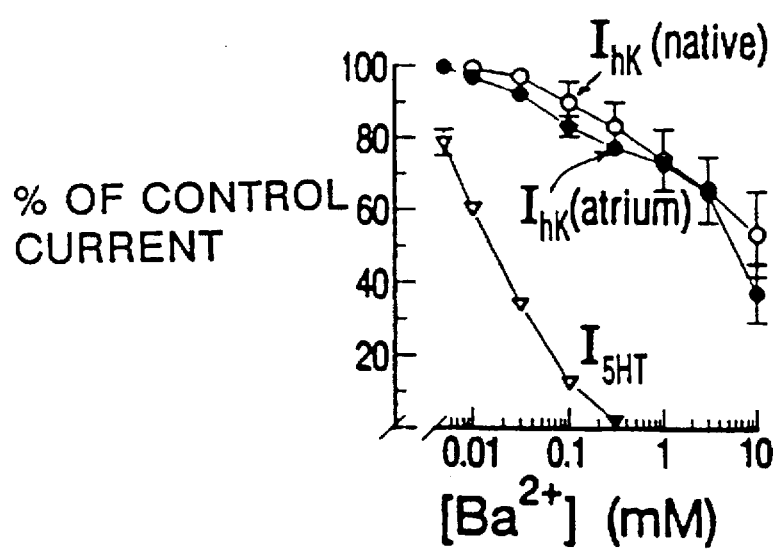

Block by external $Ba^{2+}$ is one of the characteristic features of inward rectifiers (Hille, supra.). In normal ND96 solution, $Ba^{2+}$ (5 μM-3 mM) did not cause any significant changes in resting current or conductance in native or RNA-injected oocytes at the holding potential of −80 mV. In the hK solution, $Ba^{2+}$ inhibited both $I_{hK}$ and $I_{5HT}$ (FIG. 3), and this was accompanied by a decrease in membrane conductance. 300 μM, $Ba^{2+}$ blocked about 20% of $I_{hK}$ but almost completely abolished $I_{5HT}$ (FIG. 3B). The $IC_{50}$ (half-inhibition concentration) for $Ba^{2+}$ block of $I_{5HT}$ was about 15 μM, whereas $IC_{50}$ for $I_{hK}$ block was above 3 mM (FIG. 3D). It is noteworthy that, although the sensitivity of $I_{hK}$ to $Ba^{2+}$ block was similar in native and RNA-injected oocytes, the latter did appear to have a small component of $I_{hK}$ inhibited by low doses of $Ba^{2+}$ (FIG. 3D). This raises the possibility that the atrial $I_{hK}$ is more sensitive to $Ba^{2+}$ block than the oocyte's $I_{hK}$, or that a fraction of the highly $Ba^{2+}$-sensitive channels underlying $I_{5HT}$ could be active in the absence of agonist. Note also that there was an inward current "tail" observed when $Ba^{2+}$ and 5HT was washed out simultaneously (FIG. 3B), presumably because the rate-limiting step in deactivation of the channel proceeds more slowly than unblock from $Ba^{2+}$.

To estimate the size of RNA encoding the expressed inward rectifiers, ventricle poly(A) RNA was fractionated on a sucrose gradient. The size distribution of the fractions was measured by RNA gel blots probed with [$^{32}$p]-labeled poly (T) (Lubbert et al. (1987) *J. Neurosci.* 7:1159–1165). The RNA encoding $I_{5HT}$ was found mainly in two size fractions covering the range between 2.5 and 5.5 kb. The peak expression of ventricle $I_{hK}$ was in lower size fractions, in the 1.5–3 kb range.

Figure 4A:
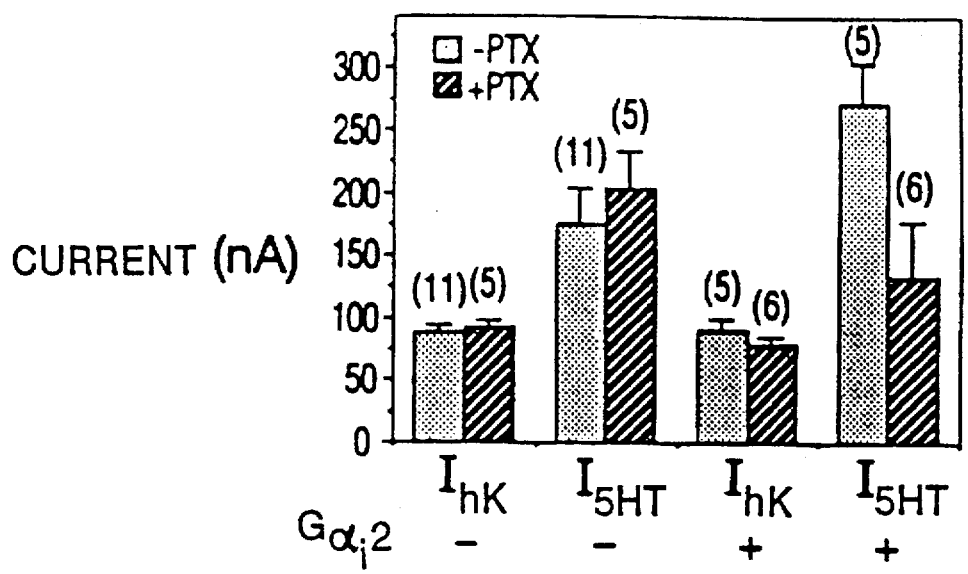
Figure 4B:
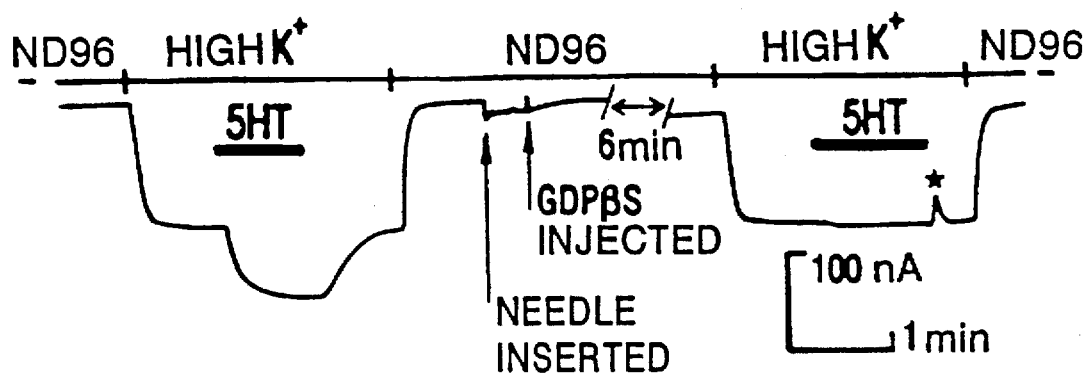

In atrium, the muscarinic receptor is coupled to the KG channel via a PTX-sensitive G-protein. Surprisingly, in RNA-injected oocytes, $I_{5HT}$ was not affected by treatment with PTX; neither was $I_{hK}$ (FIG. 4A). To test whether the 5HT1A receptor couples to the $K^+$ channel via a G-protein, the oocytes were injected with 400–800 pmole/oocyte of the non-hydrolysable analog of GDP, GDP-β-S, which is known to inhibit the activity of PTX-sensitive as well as of PTX-insensitive G-proteins (Gilman (1987) *A. Rev. Biochem.* 56:615–649). In 4 cells, GDP-β-S injection had no effect on $I_{hK}$ (115±8% of control) but strongly inhibited $I_{5HT}$, to 4±1% of control (FIG. 4B). Thus, it appears that the coupling between the 5HT1A receptor and the KG channel occurs via an oocyte's endogenous PTX-insensitive G-protein.

We examined whether an overexpressed PTX-sensitive α subunit of a G-protein, e.g. $G_{i2}α$, could compete with the "native" PTX-insensitive α subunit for the expressed 5HT1A receptor, thus restoring the PTX sensitivity of the KG channel activation. As shown in FIG. 4A, in oocytes injected with atrial RNA plus cRNAs encoding 5HT1A-R and $G_{i2}α$, PTX inhibited $I_{5HT}$ by about 50% (P<0.01, two-tailed t-test), whereas $I_{hK}$ was unaffected.

DISCUSSION

The present results demonstrate for the first time that the atrial inward rectifier $K^+$ (KG) channel, which in the native tissue is activated by ACh via a PTX-sensitive G-protein, is expressed in oocytes injected with atrial RNA. Current through the channel can be activated by acetylcholine (ACh) or, if RNA encoding a neuronal 5HT1A receptor in co-injected with atrial RNA, by serotonin (5HT). Activation of the channel probably occurs via a muscarinic ACh receptor synthesized following atrial RNA injection, rather than via the oocyte's endogenous muscarinic receptor. The latter couples to phospholipase C, and its activation induces very characteristic large transient Cl⁻ current responses caused by $Ca^{2+}$ release from intracellular stores (Dascal (1987) *CRC Crit. Rev. Biochem.* 22:317–387). Fortunately, the majority of oocyte batches lose this response after defolliculation (Miledi & Woodward (1989) *J. Physiol.* 416:601–621), and this response was not observed in the present study. Because the ACh-evoked currents were small in most cases, we concentrated on the study of the 5HT response; the latter was undoubtedly mediated by the introduced 5HT1A receptor, as 5HT was ineffective in oocytes not injected with 5HT1A-RNA, and the response displayed the expected pharmacological properties.

The evidence presented here indicates that, in oocytes injected with atrial and 5HT1A-R RNAs, activation of the 5HT1A receptor leads to opening of a $K^+$ channel that bears distinctive features of an inward rectifier, similar to those of the atrial KG: i) it conducts inward but not outward $K^+$ current; ii) it is blocked by low concentrations of $Ba^{2+}$, iii) the conductance of the channel does not depend solely on voltage but on ($E-E_K$). The expression of this channel must truly be directed by atrial RNA, because: i) no hormone or transmitter-activated current of this kind is observed in native oocytes; ii) expression of 5HT1A receptor alone does not cause the appearance of such a response. Based on ventricle RNA fractionation data, the RNA encoding the 5HT-activated channel is in a broad size range between 2.5 and 5.5 kb. This is similar or somewhat smaller than the reported 4-5 kb mRNA size of some constitutively active inward rectifiers expressed in Xenopus oocytes (Lewis et al (1991) *FEBS Lett.* 290:17–21; and Perier et al. (1992) *J. Neurochem.* 59:1971–1974), as well as of the cloned IRK1 (5.5 kb) and ROMK1 (4 kb) channels. The properties of $I_{5HT}$ directed by ventricle and atrial RNA are very similar, and it is reasonable to assume that they are encoded by the same RNA species.

Opening of the inward rectifier by 5HT is mediated by activation of a G-protein, as expected for the KG channel, because i) 5HT1A receptor belongs to the family of 7-helix receptors all of which act via Gproteins (Dascal (1987) supra.); ii) $I_{5HT}$ was inhibited by intracellular injection of GDP-β-S. However, the G-protein participating in this pathway was PTX-insensitive, possibly an endogenous oocyte G-protein. It is not clear why in the oocyte the channel activation pathway involves a PTX-insensitive G-protein. The atrial KG channel normally couples to $G_i$ (Brown & Birnbaumer, supra.), and there are at least two subspecies of $G_i$ in the oocyte (Olate et al. (1990) *FEBS Lett.* 268:27–31); also, some $G_i$ may be expressed from atrial RNA. Also, in the hippocampus, the 5HT1A receptor opens a $K^+$ channel by activating a PTX-sensitive G-protein. One possibility is that a vast excess of this undefined PTX-insensitive G-protein overrides the others in competition for coupling to the 5HT1A receptor. Whatever the reason for this unexpected coupling, our results show that the PTX sensitivity of the KG channel activation can be partially restored by overexpression of the α subunit of $G_i$. Since the actual identify of the α subunit does not seem to be important for activation of the expressed KG channel, these results imply that the βγ subunit complex doublet may be the activator of the channel in this case.

Atrial and ventricle RNAs also induce an enhanced activity of an additional inward rectifier, that is active in the absence of any specific stimulation (referred to as $I_{hK}$ herein). $I_{hK}$ in atrial RNA-injected oocytes is about twice as large as in native oocytes or oocytes injected with 5HT1A-R RNA alone. This current does not appear to represent the "basal" activity of the same channel activated by 5HT or ACh because it has a much lower sensitivity to $Ba^{2+}$ block. Moreover, the fractionation data indicates that the RNA directing the expression of $I_{hK}$ is smaller than that encoding the KG channel. However, it is not clear whether this atrial (or ventricle) RNA encodes the channel itself or a factor that enhances the expression or the activity of a native channel. Further studies, such as expression cloning, will help to identify the messages encoding the two inward rectifiers whose expression is reported here.

EXAMPLE 2

Formation of Heteromultimeric Kir3.0 Channels
Materials and Methods

Plasmids and DNAs. To isolate Kir3.2 and Kir3.3 from mouse brain RNA, oligonucleotides were designed that anneal to the first assigned methionine codon and the assigned stop codon of mouse Kir3.2 and Kir3.3 SEQ. ID NOS: 3 and 5,respectively. (Lesage et al (1994) *FEBS Lett.* 353:37–42). Kir3.0-specific sequences were coupled to a 5'-end untranslated sequence from alfalfa mosaic virus (Jobling and Gehrke (1987) *Nature* 325:622–625) and a T7 RNA polymerase recognition site to confer an optimal translational initiation site and allow RNA synthesis in vivo (cRNA). At the 3' end, a poly(A) tail was added to confer RNA stability. Total RNA from adult mouse brain (purchased from Clontech) was used as template for cDNA synthesis (Sambrook et al., supra.). PCR was conducted in a thermal cycler (Perkin-Elmer) by using Vent Polymerase (New England Biolabs), which minimizes misincorporations during the amplification step. Kir3.2 and Kir3.3 PCR-derived sequences were then inserted into the pNoTA vector (5 Prime→3 Primer, Inc.) for subsequent sequence analysis.

Kir3.1 cloned from cardiac atrium and inserted originally in pBluescript (Stratagene) was transferred to the vector MXT (gift from J. Yang; University of Texas, Dallas), in which the cloning site is flanked by 5' and 3' untranslated sequences from Xenopus globin. G protein subunits $G_{β1}$ and $G_{γ2}$ cDNAs were in the pFrogy vector (gift from L. Jan, University of California, San Francisco), as described in Lim et al. (1995) *J. Gen. Physiol.* 105:421–439. The m2R cDNA (gift from E. Peralta, Harvard University) was in the pGEM3 vector (Promega).

RNA Synthesis and Oocyte Injections. Kir3.2 and Kir3.3 cRNAs were synthesized directly from gel-isolated PCR products, while the remaining cRNAs were synthesized from linearized plasmid DNAs. cRNAs were dissolved in sterile water and injected into state V or VI Xenopus oocytes as described in Quick and Lester (1994) in *Ion Channels of Excitable Cells*, ed. Narahashi (Academic, San Diego) pp.261–279. Oocytes were maintained in ND96 solution. Oocytes were assayed 2–5 days after injection.

Electrophysiology. Whole-cell currents from oocytes were measured by using an Axoclamp 2A or Geneclamp 500 amplifier (Axon Instruments, Foster City, Calif.) in the two-electrode, voltage-clamp configuration. Current and voltage electrodes were filled with 3M KCl to yield resistances ranging from 0.5 to 1.5MΩ. Recordings were started in an external solution ($OK^+$) containing 98 mM NaCl, 1 mM $MgCl_2$, and 5 mM Hepes, pH 7.3. In high-$K^+$-containing solutions, the NaCl was replaced either completely by 98 mM KCl ($98K^+$), or partially, by 20 mM KCl ($20K^+$).

Cell-attached recordings of single channels were recorded from Xenopus oocytes as described in Methfessel et al. (1986) Pflugers Arch. 407, 577–588. Pipette solutions contained 150 mM KCl, 1 mM $CaCl_2$, and 5 mM Hepes, pH 7.3 with KOH. Bath solution contained 150 mM KCl, 1 mM $MgCl_2$, 1 mM EGTA, and 5 mM Hepes, pH 7.3 with KOH. For single-channel analysis, the current traces were filtered at 2 kHz and sampled at 10 kHz. Current amplitude histograms and open-time durations were obtained by using FETCHAN and pSTAT from pCLAMP 6.0 (Axon Instruments). All recordings were performed at room temperature (≈22° C.).

RESULTS

Kir3.1 is abundantly expressed in cardiac atrium and brain. When heterologously expressed in Xenopus oocytes, Kir3.1 induces strong inwardly rectifying $K^+$ currents either with m2R activation or with coexpression of G-protein subunits $G_{β1}$ and $G_{γ2}$.

Because expression of Kir3.2 and Kir3.1 was consistently smaller than for other channels expressed in oocytes, the effects of Kir3.1 and Kir3.2 coexpression under conditions of maximal m2R activation [1 μM acetylcholine (ACh)] were examined. With the coinjection of Kir3.1 and Kir3.2 (Kir3.1+2) cRNAs (0.5 ng each per oocyte), exposure to ACh in these oocytes led to development of large inward currents when the voltage was jumped from 0 mV to more negative values. By contrast, in oocytes injected with Kir3.2 or Kir3.1 cRNAs (1 ng), receptor activated currents were much smaller in amplitude, comparable to levels reported previously. On average, Kir3.1+2 currents [inward currents induced by ACh ($I_{K,ACh}$)=−6.4±0.8 µA; mean±SEM; n=5] were about 9-fold larger than Kir3.2 currents ($I_{K,ACh}$=−698±98 nA; n=7) and 17-fold larger than Kir3.1 currents ($I_{K,ACh}$=−365±45 nA; n=5).

Kir3.1 expressed in oocytes shows distinctive gating kinetics, including slow phases of activation (several hundred ms) during a jump from 0 mV to more negative potentials. For a similar voltage jump, Kir3.2 expressed in oocytes showed kinetics that more closely resemble other strong inward rectifiers, with a prominent phase of inactivation. These differences may be governed at least partially by differences in the sequence of the P region. The coexpressed subunits showed a slow phase of activation, but the time course of this activation cannot be explained as a simple weighted sum of the waveforms for Kir3.1 alone and Kir3.2 alone. Thus, the relations for jumps to voltages between −60 and −140 mV were well described by two exponential components with nearly voltage-independent time constants; at −80 mV the time constant of the slower component was 213±12 ms (n=4), or less than half that for Kir3.1 (32). These kinetic differences indicate molecular interactions between the Kir3.1 and Kir3.2 channels.

The large enhancement of the agonist-evoked currents for coexpressed channels might be explained by effects on any component in the receptor-channel signaling pathway, including receptors, endogenous G proteins, or the channels themselves. To discriminate among these possibilities, the receptor was uncoupled from the channel by overexpression of G protein subunits Gβ1 and Gγ2. Importantly, cells expressing Gβ1γ2 and Kir3.2 showed persistent inwardly rectifying currents at amplitudes comparable or larger to those observed for m2R activation of Kir3.2. Therefore, Kir3.2, like Kir3.1, is activated by Gβγ.

Cells coexpressing Kir3.2 and Kir3.1 (Kir3.1+2) responded to high-$K^+$ solution with much larger currents than did cells expressing only Kir3.1 or Kir3.2, consistent with the results obtained with m2R activation. On average, Kir3.1+2 currents ($I_K$=−4.3±1 µA; n=7) were 14 times larger than Kir3.2 currents ($I_K$=−305±56 nA; n=7) and 40 times larger than Kir3.1 currents ($I_K$=−104±10 NA; n=6). Thus, these experiments demonstrate that the large mutual potentiating effect of Kir3.1+2 is independent of the method of G-protein activation and argue that the effects are on the channels themselves.

An increase in the number of channels or modification of the intrinsic channel properties might account for this potentiation. Single-channel recordings of Kir3.1+2 in combination or of Kir3.2 alone were made to test these possibilities. In oocytes coinjected with cRNAs for Kir3.2, Gβ1, and Gγ2, single-channel currents in the cell-attached configuration displayed features consistent with macroscopic measurements, i.e. with hyperpolarization of the unit conductance increased. No outward currents were detected at membrane potentials positive to the $K^+$ equilibrium potential ($E_K$; ≈0 mV). These channels openings had a mean slope conductance of 30±2 pS (n=4) over the range from −40 to −100 mV, significantly smaller than the value of 39 pS for Kir3.1 alone, and showed bursts of flicker activity. Mean open-time distribution could be described by a fast component of 0.1 ms (35% of the total number of events) and a main slower component of 0.5 ms (65% of the total number of events).

The combination of Kir3.1+2 produced unitary currents with strong inward rectification and a mean slope conductance of 35±3 pS (n=4), intermediate between the values for Kir3.1 alone and Kir3.2 alone. In addition, Kir3.1+2 channels displayed markedly longer openings than Kir3.2 channels. Recordings from Kir3.1+2 channels showed a 7-fold increase in the major component of open-time duration (3.5 ms; 71% of the total number of events; there was also a smaller component of 0.5 ms; 29% of the total number of events) compared to Kir3.2. Qualitatively, the Kir3.1+2 patch recordings are rather similar to those observed for Kir3.1 in terms of mean open time, although the typically low expression levels for Kir3.1 alone vitiate systematic comparisons. At present, it is not known whether this increase, like the increase in macroscopic currents on Kir3.1+2 coexpression, is solely explained by the increase in open-time duration or whether the enhanced currents also arise from an increase in the number of openings, either because each channel opens more often or because there are more functional channels.

The effects of Kir3.3 coexpression was tested with Kir3.1 or Kir3.2. Injection of Kir3.3, Gβ$_1$, and Gγ$_2$ cRNAs did not activate inward currents in high-$K^+$-containing solution; nor were currents activated by opioid receptors. Nevertheless, Kir3.3 had profound effects when coexpressed with Kir3.1. Coexpression of Kir3.1 and Kir3.3 (Kir3.1+3) resulted in 7-fold larger $I_K$ currents ($I_K$=−3.4±0.5 µA; n=6) than for Kir3.1 alone ($I_K$=−481±43 nA; n=6). Such augmentation was seen for each of several batches of oocytes and cRNAs and on activation of the m2R pathway. Thus, these results demonstrate that Kir3.3, despite not being directly activated by G protein subunits Gβ$_1$ and Gγ$_2$, can interact with, and increase, G-protein-mediated responses of Kir3.1.

Surprisingly, Kir3.3 had a suppressing effect when coexpressed with Kir3.2. Gβγ-induced, inwardly rectifying currents in oocytes coinjected with Kir3.2 and Kir3.3 cRNAs (0.5 ng each per oocyte) ($I_K$=−129±22 nA; n=7) were much smaller than in oocytes injected with Kir3.2 cRNA alone (1 ng per oocyte) $I_K$=−5.1±0.6 µA; n=9). This dominant-negative effect of GIRk3 on Kir3.2 currents was also observed when m2R was coexpressed, instead of G-protein subunits Gβ$_1$ and Gγ$_2$.

A very important issue is raised by the occurrence of heteromultimeric channels is their differential distribution in excitable tissues and their physiological significance. Distinct Kir3.0 heteromultimeric channels may be modulated or activated by G proteins differentially, as reported for other G protein effectors. This allows for a larger degree of flexibility in the control of this important form of neuronal signaling.

The plasmid pBSIIKS(−)KGA, encoding the rat inward rectifier, G-protein activated, mammalian, potassium KGA channel was deposited on May 17, 1993 with the American Type Culture Collection (ATCC), 12301 Parklawn Drive, Rockville, Md. 20852, U.S.A., under the provisions of the Budapest Treaty for the International Recognition of the Deposition of Microorganism for the Purposes of Patent Procedure, and given the ATCC accession number 75469.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. Isolated nucleic acid comprising at least two genes, wherein each gene encodes a different inward rectifier, G-protein activated, mammalian, potassium Kir3.0 polypeptide, wherein said Kir3.0 polypeptides are characterized by their ability to cause a change in potassium flow across a Xenopus oocyte cell membrane upon their combined expression therein, and wherein each of said genes hybridizes under low stringency conditions to a complement of a nucleic acid coding for a Kir3.0 polypeptide selected from the group consisting of Kir3.1, Kir3.2, Kir3.3 and Kir3.4.

2. A nucleic acid acccording to claim 1, wherein said mammalian Kir3.0 polypeptides are Kir3.1/KGA and Kir3.2.

3. A nucleic acid acccording to claim 1, wherein said mammalian Kir3.0 polypeptides are Kir3.1/KGA and Kir3.3.

4. A nucleic acid acccording to claim 1, wherein said mammalian Kir3.0 polypeptides are Kir3.2 and Kir3.3.

5. A nucleic acid according to claim 2, wherein said Kir3.1/KGA polypeptide has the amino acid sequence of SEQ ID NO:2.

6. A method for producing a functional Kir3.0 channel in an expression host cell, the method comprising:

introducing into said expression host cell a nucleic acid encoding a first mammalian Kir3.0 polypeptide and a nucleic acid encoding a second mammalian Kir3.0 polypeptide into said expression host cell under conditions that permit expression of said nucleic acid, wherein said first and second mammalian Kir3.0 polypeptides are different from each other, and wherein the nucleic acid encoding the first mammalian Kir3.0 polypeptide and the nucleic acid encoding the second mammalian Kir3.0 polypeptide each hybridizes under low stringency conditions to a complement of a nucleic acid coding for a Kir3.0 polypeptide selected from the group consisting of Kir3.1, Kir3.2, Kir3.3 and Kir3.4; wherein said mammalian Kir3.0 polypeptides assemble to form a functional Kir3.0 in said expression host cell.

7. A method according to claim 6, wherein said nucleic acid encoding said first mammalian Kir3.0 polypeptide and said nucleic acid encoding said second mammalian Kir3.0 polypeptide are present on a single vector.

8. A method according to claim 6, wherein said nucleic acid encoding said first mammalian Kir3.0 polypeptide and said nucleic acid encoding said second mammalian Kir3.0 polypeptide are present on different vectors.

9. A method acccording to claim 6, wherein said mammalian Kir3.0 polypeptides are Kir3.1/KGA and Kir3.2.

10. A method acccording to claim 6, wherein said mammalian Kir3.0 polypeptides are Kir3.1/KGA and Kir3.3.

11. A method acccording to claim 6, wherein said mammalian Kir3.0 polypeptides are Kir3.2 and Kir3.3.

12. A host cell made by the method of claim 6.

13. A host cell acccording to claim 12, wherein said mammalian Kir3.0 polypeptides are Kir3.1/KGA and Kir3.2.

14. A host cell acccording to claim 12, wherein said mammalian Kir3.0 polypeptides are Kir3.1/KGA and Kir3.3.

15. A host cell acccording to claim 12, wherein said mammalian Kir3.0 polypeptides are Kir3.2 and Kir3.3.

16. A host cell according to claim 12, wherein said host cell is a Xenopus laevis oocyte.

17. A method for screening for agents that modulate the activity of a Kir3.0 channel, the method comprising:

providing a Kir3.0 channel formed from at least two different inward rectifier, G-protein activated, mammalian, potassium Kir3.0 polypeptides, wherein the Kir3.0 polypeptides are each formed by expression of an isolated nucleic acid which hybridizes under low stringency conditions to a complement of a nucleic acid coding for a Kir3.0 polypeptide selected from the group consisting of Kir3.1, Kir 3.2, Kir3.3 and Kir3.4;

combining a candidate agent with a functional Kir3.0 channel under conditions that permit inward $K^+$ current;

determining the induced current;

wherein a change in said induced current in the presence of said agent as compared to a control is indicative that said agent modulates the activity of a Kir3.0 channel.

18. A method for screening for agents that modulate the activity of a Kir3.0 channel, the method comprising:

providing a functional Kir3.0 channel formed in accordance with claim 6;

combining a candidate agent with a functional Kir3.0 channel under conditions that permit inward $K^+$ current;

determining the induced current;

wherein a change in said induced current in the presence of said agent as compared to a control is indicative that said agent modulates the activity of a Kir3.0 channel.

19. A screening assay for identifying materials which modulate the activity of a Kir3.0 channel, comprising the steps of:

(a) introducing nucleic acid encoding a Kir3.0 channel formed from at least two different inward rectifier, G-protein activated, mammalian, potassium Kir3.0 polypeptides, wherein the Kir3.0 polypeptides are each encoded by an isolated nucleic acid which hybridizes under low stringency conditions to a complement of a nucleic acid coding for a Kir3.0 polypeptide selected from the group consisting of Kir3.1, Kir3.2, Kir3.3 and Kir3.4, into an expression system and causing the expression system to express said nucleic acid encoding a Kir3.0 channel;

(b) contacting the Kir3.0 channel with one or more candidate channel-modulatory materials;

(c) selecting candidate material(s) which modulate said activity relative to a control performed in their absence.

* * * * *

UNITED STATES PATENT AND TRADEMARK OFFICE
CERTIFICATE OF CORRECTION

PATENT NO. : 5,744,324  Page 1 of 2
DATED : April 28, 1998
INVENTOR(S) : LESTER et al.

It is certified that error appears in the above-identified patent and that said Letters Patent is hereby corrected as shown below:

Column 1, line 50, delete "$\alpha$" and insert therefor --$\partial$--.

Column 1, line 58, delete "belongs" and insert therefor --belong--.

Column 3, line 6, delete "♦" and insert therefor --▲--.

Column 3, line 44, delete "(Kir. 0 " and insert therefor --(Kir1.0 --.

Column 4, line 18, delete "Ba2+" and insert therefor --$Ba^{2+}$--.

Column 5, line 3, delete "art" and insert therefor --an--.

Column 12, line 12, delete "$CACl_2/5$" and insert therefor --$CaCl_2/5$--.

Column 12, line 15, delete "$CACl_2/5$" and insert therefor --$CaCl_2/5$--.

Column 12, line 56, directly under "TABLE 1" insert a new paragraph to read -- Inward currents evoked by high $K^+$ and by 5HT. The entries are inward currents in nA shown as mean±SEM (n), measured at -80mV in the hK solution. 5HT concentration ranged in different experiments from 100 nM to 2$\mu$M.--

UNITED STATES PATENT AND TRADEMARK OFFICE
CERTIFICATE OF CORRECTION

PATENT NO. : 5,744,324
DATED : April 28, 1998
INVENTOR(S) : LESTER et al.

It is certified that error appears in the above-identified patent and that said Letters Patent is hereby corrected as shown below:

Column 12, line 58, Table 1, delete "$I_{nk}$" and insert therefor --$I_{hk}$--.

Column 13, line 11, delete "(n-4)" and insert therefor --(n=4)--.

Column 17, line 61, delete "30±2 pS" and insert therefor --30± 2pS--.

Signed and Sealed this

Sixth Day of October, 1998

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2070 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 32..1534

( x i ) SEQUENCE DESCRIPTION: SEQ ID NO:1:

```
GGCACGAGAA TCTGGATCTC CCCTCCGTAT T ATG TCT GCA CTC CGA AGG AAA        52
                                   Met Ser Ala Leu Arg Arg Lys
                                    1               5

TTT GGG GAC GAT TAC CAG GTA GTG ACC ACT TCG TCC AGC GGT TCG GGC      100
Phe Gly Asp Asp Tyr Gln Val Val Thr Thr Ser Ser Ser Gly Ser Gly
            10              15                  20

TTG CAG CCC CAG GGG CCA GGA CAG GGC CCA CAG CAG CAG CTT GTA CCC      148
Leu Gln Pro Gln Gly Pro Gly Gln Gly Pro Gln Gln Gln Leu Val Pro
    25                  30                  35

AAG AAG AAA CGG CAG CGG TTC GTG GAC AAG AAC GGT CGG TGC AAT GTG      196
Lys Lys Lys Arg Gln Arg Phe Val Asp Lys Asn Gly Arg Cys Asn Val
40              45                  50                  55

CAG CAC GGC AAC CTG GGC AGC GAG ACC AGT CGC TAC CTT TCC GAC CTC      244
Gln His Gly Asn Leu Gly Ser Glu Thr Ser Arg Tyr Leu Ser Asp Leu
                60                  65                  70

TTC ACT ACC CTG GTG GAT CTC AAG TGG CGT TGG AAC CTC TTT ATC TTC      292
Phe Thr Thr Leu Val Asp Leu Lys Trp Arg Trp Asn Leu Phe Ile Phe
            75                  80                  85

ATC CTC ACC TAC ACC GTG GCC TGG CTC TTC ATG GCG TCC ATG TGG TGG      340
Ile Leu Thr Tyr Thr Val Ala Trp Leu Phe Met Ala Ser Met Trp Trp
        90                  95                  100

GTG ATC GCT TAT ACC CGG GGC GAC CTG AAC AAA GCC CAT GTC GGC AAC      388
Val Ile Ala Tyr Thr Arg Gly Asp Leu Asn Lys Ala His Val Gly Asn
105                 110                 115

TAC ACT CCC TGT GTG GCC AAT GTC TAT AAC TTC CCC TCT GCC TTC CTT      436
Tyr Thr Pro Cys Val Ala Asn Val Tyr Asn Phe Pro Ser Ala Phe Leu
120                 125                 130                 135

TTC TTC ATC GAG ACC GAG GCC ACC ATC GGC TAT GGC TAC CGC TAC ATC      484
Phe Phe Ile Glu Thr Glu Ala Thr Ile Gly Tyr Gly Tyr Arg Tyr Ile
                140                 145                 150

ACC GAC AAG TGC CCC GAG GGC ATC ATC CTT TTC CTT TTC CAG TCC ATC      532
Thr Asp Lys Cys Pro Glu Gly Ile Ile Leu Phe Leu Phe Gln Ser Ile
            155                 160                 165

CTT GGC TCC ATC GTG GAC GCT TTC CTC ATC GGC TGC ATG TTC ATC AAG      580
Leu Gly Ser Ile Val Asp Ala Phe Leu Ile Gly Cys Met Phe Ile Lys
        170                 175                 180

ATG TCC CAG CCC AAA AAG CGC GCC GAG ACC CTC ATG TTT AGC GAG CAT      628
Met Ser Gln Pro Lys Lys Arg Ala Glu Thr Leu Met Phe Ser Glu His
185                 190                 195

GCG GTT ATT TCC ATG AGG GAC GGA AAA CTC ACT CTC ATG TTC CGG GTG      676
Ala Val Ile Ser Met Arg Asp Gly Lys Leu Thr Leu Met Phe Arg Val
200                 205                 210                 215
```

| | | | | | | | | | | | | | | | | |
|---|---|---|---|---|---|---|---|---|---|---|---|---|---|---|---|---|
| GGC | AAC | CTG | CGC | AAC | AGC | CAC | ATG | GTC | TCC | GCG | CAG | ATC | CGC | TGC | AAG | 724 |
| Gly | Asn | Leu | Arg | Asn | Ser | His | Met | Val | Ser | Ala | Gln | Ile | Arg | Cys | Lys | |
| | | | 220 | | | | | 225 | | | | | 230 | | | |
| CTG | CTC | AAA | TCT | CGG | CAG | ACA | CCT | GAG | GGT | GAG | TTT | CTA | CCC | CTT | GAC | 772 |
| Leu | Leu | Lys | Ser | Arg | Gln | Thr | Pro | Glu | Gly | Glu | Phe | Leu | Pro | Leu | Asp | |
| | | | 235 | | | | | 240 | | | | | 245 | | | |
| CAA | CTT | GAA | CTG | GAT | GTA | GGT | TTT | AGT | ACA | GGG | GCA | GAT | CAA | CTT | TTT | 820 |
| Gln | Leu | Glu | Leu | Asp | Val | Gly | Phe | Ser | Thr | Gly | Ala | Asp | Gln | Leu | Phe | |
| | | 250 | | | | | 255 | | | | | 260 | | | | |
| CTT | GTG | TCC | CCT | CTC | ACC | ATT | TGC | CAC | GTG | ATC | GAT | GCC | AAA | AGC | CCC | 868 |
| Leu | Val | Ser | Pro | Leu | Thr | Ile | Cys | His | Val | Ile | Asp | Ala | Lys | Ser | Pro | |
| | 265 | | | | | 270 | | | | | 275 | | | | | |
| TTT | TAT | GAC | CTA | TCC | CAG | CGA | AGC | ATG | CAA | ACT | GAA | CAG | TTC | GAG | GTG | 916 |
| Phe | Tyr | Asp | Leu | Ser | Gln | Arg | Ser | Met | Gln | Thr | Glu | Gln | Phe | Glu | Val | |
| 280 | | | | | 285 | | | | | 290 | | | | | 295 | |
| GTC | GTC | ATC | CTG | GAA | GGC | ATC | GTG | GAA | ACC | ACA | GGG | ATG | ACT | TGT | CAA | 964 |
| Val | Val | Ile | Leu | Glu | Gly | Ile | Val | Glu | Thr | Thr | Gly | Met | Thr | Cys | Gln | |
| | | | | 300 | | | | | 305 | | | | | 310 | | |
| GCT | CGA | ACA | TCA | TAC | ACC | GAA | GAT | GAA | GTT | CTT | TGG | GGT | CAT | CGT | TTT | 1012 |
| Ala | Arg | Thr | Ser | Tyr | Thr | Glu | Asp | Glu | Val | Leu | Trp | Gly | His | Arg | Phe | |
| | | | 315 | | | | | 320 | | | | | 325 | | | |
| TTC | CCT | GTA | ATT | TCT | TTA | GAA | GAA | GGA | TTC | TTT | AAA | GTC | GAT | TAC | TCC | 1060 |
| Phe | Pro | Val | Ile | Ser | Leu | Glu | Glu | Gly | Phe | Phe | Lys | Val | Asp | Tyr | Ser | |
| | | 330 | | | | | 335 | | | | | 340 | | | | |
| CAG | TTC | CAT | GCA | ACC | TTT | GAA | GTC | CCC | ACC | CCT | CCG | TAC | AGT | GTG | AAA | 1108 |
| Gln | Phe | His | Ala | Thr | Phe | Glu | Val | Pro | Thr | Pro | Pro | Tyr | Ser | Val | Lys | |
| | 345 | | | | | 350 | | | | | 355 | | | | | |
| GAG | CAG | GAA | GAA | ATG | CTT | CTC | ATG | TCT | TCC | CCT | TTA | ATA | GCA | CCA | GCC | 1156 |
| Glu | Gln | Glu | Glu | Met | Leu | Leu | Met | Ser | Ser | Pro | Leu | Ile | Ala | Pro | Ala | |
| 360 | | | | | 365 | | | | | 370 | | | | | 375 | |
| ATA | ACC | AAC | AGC | AAA | GAA | AGA | CAC | AAT | TCT | GTG | GAG | TGC | TTA | GAT | GGA | 1204 |
| Ile | Thr | Asn | Ser | Lys | Glu | Arg | His | Asn | Ser | Val | Glu | Cys | Leu | Asp | Gly | |
| | | | | 380 | | | | | 385 | | | | | 390 | | |
| CTA | GAT | GAC | ATT | AGC | ACA | AAA | CTT | CCA | TCG | AAG | CTG | CAG | AAA | ATT | ACG | 1252 |
| Leu | Asp | Asp | Ile | Ser | Thr | Lys | Leu | Pro | Ser | Lys | Leu | Gln | Lys | Ile | Thr | |
| | | | 395 | | | | | 400 | | | | | 405 | | | |
| GGG | AGA | GAA | GAC | TTT | CCC | AAA | AAA | CTC | CTG | AGG | ATG | AGT | TCT | ACA | ACT | 1300 |
| Gly | Arg | Glu | Asp | Phe | Pro | Lys | Lys | Leu | Leu | Arg | Met | Ser | Ser | Thr | Thr | |
| | | 410 | | | | | 415 | | | | | 420 | | | | |
| TCA | GAA | AAA | GCC | TAT | AGT | TTG | GGT | GAT | TTG | CCC | ATG | AAA | CTC | CAA | CGA | 1348 |
| Ser | Glu | Lys | Ala | Tyr | Ser | Leu | Gly | Asp | Leu | Pro | Met | Lys | Leu | Gln | Arg | |
| | 425 | | | | | 430 | | | | | 435 | | | | | |
| ATA | AGT | TCG | GTT | CCT | GGC | AAC | TCT | GAA | GAA | AAA | CTG | GTA | TCT | AAA | ACC | 1396 |
| Ile | Ser | Ser | Val | Pro | Gly | Asn | Ser | Glu | Glu | Lys | Leu | Val | Ser | Lys | Thr | |
| 440 | | | | | 445 | | | | | 450 | | | | | 455 | |
| ACC | AAG | ATG | TTA | TCA | GAT | CCC | ATG | AGC | CAG | TCT | GTG | GCC | GAT | TTG | CCA | 1444 |
| Thr | Lys | Met | Leu | Ser | Asp | Pro | Met | Ser | Gln | Ser | Val | Ala | Asp | Leu | Pro | |
| | | | | 460 | | | | | 465 | | | | | 470 | | |
| CCG | AAG | CTT | CAA | AAG | ATG | GCT | GGA | GGA | CCT | ACC | AGG | ATG | GAA | GGG | AAT | 1492 |
| Pro | Lys | Leu | Gln | Lys | Met | Ala | Gly | Gly | Pro | Thr | Arg | Met | Glu | Gly | Asn | |
| | | | 475 | | | | | 480 | | | | | 485 | | | |
| CTT | CCA | GCC | AAA | CTA | AGA | AAA | ATG | AAC | TCT | GAC | CGC | TTC | ACA | | | 1534 |
| Leu | Pro | Ala | Lys | Leu | Arg | Lys | Met | Asn | Ser | Asp | Arg | Phe | Thr | | | |
| | | 490 | | | | | 495 | | | | | 500 | | | | |

| | | | |
|---|---|---|---|
| TAGCAAAACA | CCCCATTAGG | CATTATTTCA | TGTTTTGATT | TAGTTTTAGT | CCAATATTTG | 1594 |
| GCTGATAAGA | TAATCCTCCC | CGGGAAATCT | GAGAGGTCTA | TCCCAGTCTG | GCAAATTCAT | 1654 |
| CAGAGGACTC | TTCATTGAAG | TGTTGTTACT | GTGTTGAACA | TGAGTTACAA | AGGGAGGACA | 1714 |
| TCATAAGAAA | GCTAATAGTT | GGCATGTATT | ATCACATCAA | GCATGCAATA | ATGTGCAAAT | 1774 |

-continued

```
TTTGCATTTA GTTTCTGGC ATGATTTATA TATGGCATAT TTATATTGAA TATTCTGGAA      1834

AAATATATAA ATATATATTT GAAGTGGAGA TATTCTCCCC ATAATTTCTA ATATATGTAT      1894

TAAGCCAAAC ATGAGTGGAT AGCTTTCAGG GCACTAAAAT AATATACATG CATACATACA      1954

TACATGCATA TGCACAGACA CATACACACA CATACTCATA TATATAAAC ATACCCATAC       2014

AAACATATAT ATCTAATAAA AATTGTGATG TTTTGTTCAA AAAAAAAAAA AAAAAA          2070
```

( 2 ) INFORMATION FOR SEQ ID NO:2:

( i ) SEQUENCE CHARACTERISTICS:
    ( A ) LENGTH: 501 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Ser Ala Leu Arg Arg Lys Phe Gly Asp Asp Tyr Gln Val Val Thr
 1               5                  10                  15

Thr Ser Ser Ser Gly Ser Gly Leu Gln Pro Gln Gly Pro Gly Gln Gly
                20                  25                  30

Pro Gln Gln Gln Leu Val Pro Lys Lys Arg Gln Arg Phe Val Asp
            35                  40                  45

Lys Asn Gly Arg Cys Asn Val Gln His Gly Asn Leu Gly Ser Glu Thr
        50                  55                  60

Ser Arg Tyr Leu Ser Asp Leu Phe Thr Thr Leu Val Asp Leu Lys Trp
65                  70                  75                  80

Arg Trp Asn Leu Phe Ile Phe Ile Leu Thr Tyr Thr Val Ala Trp Leu
                85                  90                  95

Phe Met Ala Ser Met Trp Trp Val Ile Ala Tyr Thr Arg Gly Asp Leu
               100                 105                 110

Asn Lys Ala His Val Gly Asn Tyr Thr Pro Cys Val Ala Asn Val Tyr
           115                 120                 125

Asn Phe Pro Ser Ala Phe Leu Phe Phe Ile Glu Thr Glu Ala Thr Ile
       130                 135                 140

Gly Tyr Gly Tyr Arg Tyr Ile Thr Asp Lys Cys Pro Glu Gly Ile Ile
145                 150                 155                 160

Leu Phe Leu Phe Gln Ser Ile Leu Gly Ser Ile Val Asp Ala Phe Leu
               165                 170                 175

Ile Gly Cys Met Phe Ile Lys Met Ser Gln Pro Lys Lys Arg Ala Glu
           180                 185                 190

Thr Leu Met Phe Ser Glu His Ala Val Ile Ser Met Arg Asp Gly Lys
       195                 200                 205

Leu Thr Leu Met Phe Arg Val Gly Asn Leu Arg Asn Ser His Met Val
   210                 215                 220

Ser Ala Gln Ile Arg Cys Lys Leu Leu Lys Ser Arg Gln Thr Pro Glu
225                 230                 235                 240

Gly Glu Phe Leu Pro Leu Asp Gln Leu Glu Leu Asp Val Gly Phe Ser
               245                 250                 255

Thr Gly Ala Asp Gln Leu Phe Leu Val Ser Pro Leu Thr Ile Cys His
           260                 265                 270

Val Ile Asp Ala Lys Ser Pro Phe Tyr Asp Leu Ser Gln Arg Ser Met
       275                 280                 285

Gln Thr Glu Gln Phe Glu Val Val Val Ile Leu Glu Gly Ile Val Glu
   290                 295                 300

Thr Thr Gly Met Thr Cys Gln Ala Arg Thr Ser Tyr Thr Glu Asp Glu
```

|     |     |     |     | 305 |     |     |     |     | 310 |     |     |     |     | 315 |     |     |     |     | 320 |
|-----|-----|-----|-----|-----|-----|-----|-----|-----|-----|-----|-----|-----|-----|-----|-----|-----|-----|-----|-----|
| Val | Leu | Trp | Gly | His | Arg | Phe | Phe | Pro | Val | Ile | Ser | Leu | Glu | Glu | Gly |
|     |     |     |     | 325 |     |     |     |     | 330 |     |     |     |     | 335 |     |
| Phe | Phe | Lys | Val | Asp | Tyr | Ser | Gln | Phe | His | Ala | Thr | Phe | Glu | Val | Pro |
|     |     |     | 340 |     |     |     |     | 345 |     |     |     | 350 |     |     |     |
| Thr | Pro | Pro | Tyr | Ser | Val | Lys | Glu | Gln | Glu | Glu | Met | Leu | Leu | Met | Ser |
|     |     | 355 |     |     |     |     | 360 |     |     |     |     | 365 |     |     |     |
| Ser | Pro | Leu | Ile | Ala | Pro | Ala | Ile | Thr | Asn | Ser | Lys | Glu | Arg | His | Asn |
|     |     | 370 |     |     |     | 375 |     |     |     |     | 380 |     |     |     |     |
| Ser | Val | Glu | Cys | Leu | Asp | Gly | Leu | Asp | Asp | Ile | Ser | Thr | Lys | Leu | Pro |
| 385 |     |     |     |     | 390 |     |     |     |     | 395 |     |     |     |     | 400 |
| Ser | Lys | Leu | Gln | Lys | Ile | Thr | Gly | Arg | Glu | Asp | Phe | Pro | Lys | Lys | Leu |
|     |     |     |     | 405 |     |     |     |     | 410 |     |     |     |     | 415 |     |
| Leu | Arg | Met | Ser | Ser | Thr | Thr | Ser | Glu | Lys | Ala | Tyr | Ser | Leu | Gly | Asp |
|     |     |     | 420 |     |     |     |     | 425 |     |     |     |     | 430 |     |     |
| Leu | Pro | Met | Lys | Leu | Gln | Arg | Ile | Ser | Ser | Val | Pro | Gly | Asn | Ser | Glu |
|     |     | 435 |     |     |     |     | 440 |     |     |     |     | 445 |     |     |     |
| Glu | Lys | Leu | Val | Ser | Lys | Thr | Thr | Lys | Met | Leu | Ser | Asp | Pro | Met | Ser |
|     | 450 |     |     |     |     | 455 |     |     |     |     | 460 |     |     |     |     |
| Gln | Ser | Val | Ala | Asp | Leu | Pro | Pro | Lys | Leu | Gln | Lys | Met | Ala | Gly | Gly |
| 465 |     |     |     |     | 470 |     |     |     |     | 475 |     |     |     |     | 480 |
| Pro | Thr | Arg | Met | Glu | Gly | Asn | Leu | Pro | Ala | Lys | Leu | Arg | Lys | Met | Asn |
|     |     |     |     | 485 |     |     |     |     | 490 |     |     |     |     | 495 |     |
| Ser | Asp | Arg | Phe | Thr |
|     |     |     |     | 500 |

(2) INFORMATION FOR SEQ ID NO:3:

(i) SEQUENCE CHARACTERISTICS:
        (A) LENGTH: 1978 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 488..1729

(xi) SEQUENCE DESCRIPTION: SEQ ID NO:3:

| | | | | | |
|---|---|---|---|---|---|
| GTCTCCCTGC | AAGGTCTATC | ACTTTGCTCC | TAAACGAGGA | TTTATTCCCT | CTGCCACTCA | 60 |
| AGGCTGTCCC | CCAGTTTCCT | CGCAACCGGG | CTTCCTCCTC | AGTCCCTGCC | CACACGCGCA | 120 |
| CTCCTCTGCC | CCGCGGTGGC | CCCAGCGCCC | AGCCCTCCAG | CCAGAGGGAG | CCAGGCACCA | 180 |
| GACGGCAGCA | CCTGGCTGGA | GAGGTTGGGC | GGGCCGAGGG | TGGGGATCCG | CGGGAACCGG | 240 |
| CGAGTCGGAG | CTGGAGCAGG | AGCTGGACCC | AACCGCTAGC | AGCAGAATGG | AGTCTCCTGA | 300 |
| AAGCCTGCCG | GGGCTGATGT | GAAATTGGGC | CATCTGCTTC | CAGTTGGTCT | GTTTCCTCCT | 360 |
| TTTCTTGTAT | TTTCTTCCCT | CGCCATTCAC | CGTGGAGTGA | ATTATTGAAT | CTTGCTCCGT | 420 |
| TCCGAGAGAG | GCGATCAGGA | TGGAGTGAAC | CTACCCTGTC | CACTACAAGG | AAAAGCACAA | 480 |

| AGAAGAA | ATG | ACA | ATG | GCC | AAG | TTA | ACT | GAA | TCC | ATG | ACT | AAC | GTC | TTG | 529 |
|---|---|---|---|---|---|---|---|---|---|---|---|---|---|---|---|
| | Met | Thr | Met | Ala | Lys | Leu | Thr | Glu | Ser | Met | Thr | Asn | Val | Leu | |
| | 1 | | | | 5 | | | | | 10 | | | | | |

| GAA | GGC | GAT | TCC | ATG | GAC | CAG | GAT | GTG | GAA | AGC | CCA | GTG | GCC | ATT | CAC | 577 |
|---|---|---|---|---|---|---|---|---|---|---|---|---|---|---|---|---|
| Glu | Gly | Asp | Ser | Met | Asp | Gln | Asp | Val | Glu | Ser | Pro | Val | Ala | Ile | His |
| 15 | | | | 20 | | | | | 25 | | | | | 30 |

| CAG | CCA | AAG | TTG | CCT | AAG | CAG | GCC | AGG | GAC | GAC | CTG | CCG | AGA | CAC | ATC | 625 |

```
Gln Pro Lys Leu Pro Lys Gln Ala Arg Asp Asp Leu Pro Arg His Ile
            35                  40                  45

AGC CGA GAC AGG ACC AAA AGG AAA ATC CAG AGG TAC GTG AGG AAG GAT      673
Ser Arg Asp Arg Thr Lys Arg Lys Ile Gln Arg Tyr Val Arg Lys Asp
            50                  55                  60

GGG AAG TGC AAC GTT CAC CAC GGC AAT GTG CGG GAG ACC TAC CGA TAC      721
Gly Lys Cys Asn Val His His Gly Asn Val Arg Glu Thr Tyr Arg Tyr
            65                  70                  75

CTG ACG GAC ATC TTC ACC ACC CTG GTG GAC CTG AAG TGG AGA TTC AAC      769
Leu Thr Asp Ile Phe Thr Thr Leu Val Asp Leu Lys Trp Arg Phe Asn
        80                  85                  90

CTG TTG ATC TTT GTC ATG GTC TAC ACA GTG ACG TGG CTT TTC TTT GGG      817
Leu Leu Ile Phe Val Met Val Tyr Thr Val Thr Trp Leu Phe Phe Gly
 95                 100                 105                 110

ATG ATC TGG TGG CTG ATT GCG TAC ATC CGG GGA GAT ATG GAC CAC ATA      865
Met Ile Trp Trp Leu Ile Ala Tyr Ile Arg Gly Asp Met Asp His Ile
                115                 120                 125

GAG GAC CCC TCG TGG ACT CCT TGT GTC ACC AAC CTC AAC GGG TTT GTC      913
Glu Asp Pro Ser Trp Thr Pro Cys Val Thr Asn Leu Asn Gly Phe Val
            130                 135                 140

TCT GCT TTT TTA TTC TCC ATA GAG ACA GAA ACC ACC ATC GGT TAT GGC      961
Ser Ala Phe Leu Phe Ser Ile Glu Thr Glu Thr Thr Ile Gly Tyr Gly
            145                 150                 155

TAC CGG GTC ATC ACG GAC AAG TGC CCT GAG GGG ATT ATT CTC CTC TTA     1009
Tyr Arg Val Ile Thr Asp Lys Cys Pro Glu Gly Ile Ile Leu Leu Leu
            160                 165                 170

ATC CAG TCC GTG TTG GGG TCC ATT GTC AAC GCC TTC ATG GTA GGA TGT     1057
Ile Gln Ser Val Leu Gly Ser Ile Val Asn Ala Phe Met Val Gly Cys
175                 180                 185                 190

ATG TTT GTG AAA ATA TCC CAA CCC AAG AAG AGG GCA GAG ACC CTG GTC     1105
Met Phe Val Lys Ile Ser Gln Pro Lys Lys Arg Ala Glu Thr Leu Val
                195                 200                 205

TTT TCC ACC CAC GCG GTG ATC TCC ATG CGG GAT GGG AAA CTG TGC TTG     1153
Phe Ser Thr His Ala Val Ile Ser Met Arg Asp Gly Lys Leu Cys Leu
            210                 215                 220

ATG TTC CGG GTG GGG GAC TTG AGG AAT TCT CAC ATT GTG GAG GCA TCC     1201
Met Phe Arg Val Gly Asp Leu Arg Asn Ser His Ile Val Glu Ala Ser
            225                 230                 235

ATC AGA GCC AAG TTG ATC AAG TCC AAA CAG ACT TCA GAG GGG GAG TTT     1249
Ile Arg Ala Lys Leu Ile Lys Ser Lys Gln Thr Ser Glu Gly Glu Phe
            240                 245                 250

ATT CCC CTC AAC CAG AGT GAT ATC AAC GTG GGG TAC TAC ACA GGG GAC     1297
Ile Pro Leu Asn Gln Ser Asp Ile Asn Val Gly Tyr Tyr Thr Gly Asp
255                 260                 265                 270

GAC CGG CTC TTT CTG GTG TCA CCA TTG ATT ATT AGC CAT GAA ATT AAC     1345
Asp Arg Leu Phe Leu Val Ser Pro Leu Ile Ile Ser His Glu Ile Asn
            275                 280                 285

CAA CAG AGT CCC TTC TGG GAG ATC TCC AAA GCG CAG CTG CCT AAA GAG     1393
Gln Gln Ser Pro Phe Trp Glu Ile Ser Lys Ala Gln Leu Pro Lys Glu
            290                 295                 300

GAA CTG GAG ATT GTG GTC ATC CTG GAG GGA ATC GTG GAA GCC ACA GGA     1441
Glu Leu Glu Ile Val Val Ile Leu Glu Gly Ile Val Glu Ala Thr Gly
            305                 310                 315

ATG ACG TGC CAA GCC CGA AGC TCC TAC ATC ACC AGT GAG ATC TTG TGG     1489
Met Thr Cys Gln Ala Arg Ser Ser Tyr Ile Thr Ser Glu Ile Leu Trp
            320                 325                 330

GGT TAC CGG TTC ACA CCT GTC CTA ACG ATG GAA GAC GGG TTC TAC GAA     1537
Gly Tyr Arg Phe Thr Pro Val Leu Thr Met Glu Asp Gly Phe Tyr Glu
335                 340                 345                 350

GTT GAC TAC AAC AGC TTC CAT GAG ACC TAT GAG ACC AGC ACC CCG TCC     1585
```

|     |     |     |     |     |     |     |     |     |     |     |     |     |     |     |      |
|-----|-----|-----|-----|-----|-----|-----|-----|-----|-----|-----|-----|-----|-----|-----|------|
| Val | Asp | Tyr | Asn | Ser | Phe | His | Glu | Thr | Tyr | Glu | Thr | Ser | Thr | Pro | Ser  |
|     |     |     |     | 355 |     |     |     | 360 |     |     |     |     |     | 365 |      |
| CTT | AGT | GCC | AAA | GAG | CTA | GCG | GAG | CTG | GCT | AAC | CGG | GCA | GAG | GTG | CCT  | 1633
| Leu | Ser | Ala | Lys | Glu | Leu | Ala | Glu | Leu | Ala | Asn | Arg | Ala | Glu | Val | Pro  |
|     |     |     | 370 |     |     |     |     | 375 |     |     |     |     | 380 |     |      |
| CTG | AGT | TGG | TCT | GTG | TCC | AGC | AAA | CTG | AAC | CAA | CAT | GCA | GAA | TTG | GAG  | 1681
| Leu | Ser | Trp | Ser | Val | Ser | Ser | Lys | Leu | Asn | Gln | His | Ala | Glu | Leu | Glu  |
|     |     | 385 |     |     |     |     | 390 |     |     |     |     | 395 |     |     |      |
| ACA | GAA | GAG | GAA | GAG | AAG | AAC | CCG | GAA | GAA | CTG | ACG | GAG | AGG | AAT | GGG  | 1729
| Thr | Glu | Glu | Glu | Glu | Lys | Asn | Pro | Glu | Glu | Leu | Thr | Glu | Arg | Asn | Gly  |
|     |     | 400 |     |     |     |     | 405 |     |     |     |     | 410 |     |     |      |

| TGATGCTGGG | CTCCTAGTGT | GGATCAAGAA | GTGTTCCTTC | TAAGCTCATC | CTCTGACAGA | 1789 |
| CATTACAGAG | AACTGATATA | TTTTTCCTCC | TTCACTGCTT | GGAAGAATTC | ACCCAGAATT | 1849 |
| CACCCACCCC | ATCTGGACCT | AGTACATTCT | GTTTGGGAAG | GTCATCATTA | ATTTTACTTA | 1909 |
| AAGTCGGCGC | TGGAGAGATG | ACGCCGCGGG | CTAAGATGGT | TTATTGTTCT | TGCAGACGGC | 1969 |
| CTGGGTTCA  |            |            |            |            |            | 1978 |

( 2 ) INFORMATION FOR SEQ ID NO:4:

( i ) SEQUENCE CHARACTERISTICS:
        ( A ) LENGTH: 414 amino acids
        ( B ) TYPE: amino acid
        ( D ) TOPOLOGY: linear ( ii ) MOLECULE TYPE: protein ( x i ) SEQUENCE DESCRIPTION: SEQ ID NO:4:

| Met | Thr | Met | Ala | Lys | Leu | Thr | Glu | Ser | Met | Thr | Asn | Val | Leu | Glu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asp | Ser | Met | Asp | Gln | Asp | Val | Glu | Ser | Pro | Val | Ala | Ile | His | Gln | Pro |
|     |     |     | 20  |     |     |     |     | 25  |     |     |     |     | 30  |     |     |
| Lys | Leu | Pro | Lys | Gln | Ala | Arg | Asp | Asp | Leu | Pro | Arg | His | Ile | Ser | Arg |
|     |     | 35  |     |     |     |     | 40  |     |     |     |     | 45  |     |     |     |
| Asp | Arg | Thr | Lys | Arg | Lys | Ile | Gln | Arg | Tyr | Val | Arg | Lys | Asp | Gly | Lys |
|     | 50  |     |     |     |     | 55  |     |     |     |     | 60  |     |     |     |     |
| Cys | Asn | Val | His | His | Gly | Asn | Val | Arg | Glu | Thr | Tyr | Arg | Tyr | Leu | Thr |
| 65  |     |     |     |     | 70  |     |     |     |     | 75  |     |     |     |     | 80  |
| Asp | Ile | Phe | Thr | Thr | Leu | Val | Asp | Leu | Lys | Trp | Arg | Phe | Asn | Leu | Leu |
|     |     |     |     | 85  |     |     |     |     | 90  |     |     |     |     | 95  |     |
| Ile | Phe | Val | Met | Val | Tyr | Thr | Val | Thr | Trp | Leu | Phe | Phe | Gly | Met | Ile |
|     |     |     | 100 |     |     |     |     | 105 |     |     |     |     | 110 |     |     |
| Trp | Trp | Leu | Ile | Ala | Tyr | Ile | Arg | Gly | Asp | Met | Asp | His | Ile | Glu | Asp |
|     |     | 115 |     |     |     |     | 120 |     |     |     |     | 125 |     |     |     |
| Pro | Ser | Trp | Thr | Pro | Cys | Val | Thr | Asn | Leu | Asn | Gly | Phe | Val | Ser | Ala |
|     | 130 |     |     |     |     | 135 |     |     |     |     | 140 |     |     |     |     |
| Phe | Leu | Phe | Ser | Ile | Glu | Thr | Glu | Thr | Thr | Ile | Gly | Tyr | Gly | Tyr | Arg |
| 145 |     |     |     |     | 150 |     |     |     |     | 155 |     |     |     |     | 160 |
| Val | Ile | Thr | Asp | Lys | Cys | Pro | Glu | Gly | Ile | Ile | Leu | Leu | Leu | Ile | Gln |
|     |     |     |     | 165 |     |     |     |     | 170 |     |     |     |     | 175 |     |
| Ser | Val | Leu | Gly | Ser | Ile | Val | Asn | Ala | Phe | Met | Val | Gly | Cys | Met | Phe |
|     |     |     | 180 |     |     |     |     | 185 |     |     |     |     | 190 |     |     |
| Val | Lys | Ile | Ser | Gln | Pro | Lys | Lys | Arg | Ala | Glu | Thr | Leu | Val | Phe | Ser |
|     |     | 195 |     |     |     |     | 200 |     |     |     |     | 205 |     |     |     |
| Thr | His | Ala | Val | Ile | Ser | Met | Arg | Asp | Gly | Lys | Leu | Cys | Leu | Met | Phe |
|     | 210 |     |     |     |     | 215 |     |     |     |     | 220 |     |     |     |     |
| Arg | Val | Gly | Asp | Leu | Arg | Asn | Ser | His | Ile | Val | Glu | Ala | Ser | Ile | Arg |

```
                      225                         230                         235                         240
Ala  Lys  Leu  Ile  Lys  Ser  Lys  Gln  Thr  Ser  Glu  Gly  Glu  Phe  Ile  Pro
                    245                         250                         255
Leu  Asn  Gln  Ser  Asp  Ile  Asn  Val  Gly  Tyr  Tyr  Thr  Gly  Asp  Asp  Arg
               260                         265                         270
Leu  Phe  Leu  Val  Ser  Pro  Leu  Ile  Ile  Ser  His  Glu  Ile  Asn  Gln  Gln
          275                         280                         285
Ser  Pro  Phe  Trp  Glu  Ile  Ser  Lys  Ala  Gln  Leu  Pro  Lys  Glu  Glu  Leu
     290                         295                         300
Glu  Ile  Val  Val  Ile  Leu  Glu  Gly  Ile  Val  Glu  Ala  Thr  Gly  Met  Thr
305                         310                         315                         320
Cys  Gln  Ala  Arg  Ser  Ser  Tyr  Ile  Thr  Ser  Glu  Ile  Leu  Trp  Gly  Tyr
                    325                         330                         335
Arg  Phe  Thr  Pro  Val  Leu  Thr  Met  Glu  Asp  Gly  Phe  Tyr  Glu  Val  Asp
               340                         345                         350
Tyr  Asn  Ser  Phe  His  Glu  Thr  Tyr  Glu  Thr  Ser  Thr  Pro  Ser  Leu  Ser
          355                         360                         365
Ala  Lys  Glu  Leu  Ala  Glu  Leu  Ala  Asn  Arg  Ala  Glu  Val  Pro  Leu  Ser
     370                         375                         380
Trp  Ser  Val  Ser  Ser  Lys  Leu  Asn  Gln  His  Ala  Glu  Leu  Glu  Thr  Glu
385                         390                         395                         400
Glu  Glu  Glu  Lys  Asn  Pro  Glu  Glu  Leu  Thr  Glu  Arg  Asn  Gly
                    405                         410
```

(2) INFORMATION FOR SEQ ID NO:5:

(i) SEQUENCE CHARACTERISTICS:
        (A) LENGTH: 2301 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 308..1435

(xi) SEQUENCE DESCRIPTION: SEQ ID NO:5:

```
CTGAGCTGCC GTTACATTCA GGAGAAACAG CAGTGTCGGC GGCTCCCAAT CTCAGAGGGA      60

ACCTAGGGTA CTGGGGAGA  TGGTGTCAGG GACATGGACG CCAACCCCCA AGGGTTTCTG     120

CTGCTGGCTA CTCTTCTCTC CAGGCTCTAC TTCTGTTCAT ACGGTCCATA TCTCCTAGGG     180

GACCCTGAAA GCCTAGGAAC CGACTCTGGC CATCCATCTC TCCGGGAAGA TTATAACCCA     240

GAGTGCTTCT CAGGGGGGAA GAATTTGAAG CAAAACCAGA CCCCGCAGGA TCCCCGCTGC     300

GGCCGCC ATG GCG CAG GAG AAC GCC GCT TTC TCT CCC GGG TCG GAG GAG       349
        Met Ala Gln Glu Asn Ala Ala Phe Ser Pro Gly Ser Glu Glu
        1               5                   10

CCG CCA CGC CGC CGC GGT CGC CAG CGC TAC GTG GAG AAG GAC GGT CGC       397
Pro Pro Arg Arg Arg Gly Arg Gln Arg Tyr Val Glu Lys Asp Gly Arg
15                  20                  25                  30

TGT AAC GTG CAG CAG GGC AAC GTC CGC GAG ACC TAC CGC TAC CTG ACC       445
Cys Asn Val Gln Gln Gly Asn Val Arg Glu Thr Tyr Arg Tyr Leu Thr
                35                  40                  45

GAC CTG TTC ACC ACG CTG GTG GAC CTG CAG TGG CGC CTC AGA CTG CTC       493
Asp Leu Phe Thr Thr Leu Val Asp Leu Gln Trp Arg Leu Arg Leu Leu
            50                  55                  60

TTC TTC GTG CTC GCC TAC GCG CTC ACT TGG CTC TTC TTC GGT GTC ATC       541
Phe Phe Val Leu Ala Tyr Ala Leu Thr Trp Leu Phe Phe Gly Val Ile
        65                  70                  75
```

| | | | | | | | | | | | | | | | | |
|---|---|---|---|---|---|---|---|---|---|---|---|---|---|---|---|---|
| TGG | TGG | CTC | ATC | GCC | TAC | GGT | CGC | GGC | GAC | CTG | GAG | CAC | CTG | GAG | GAC | 589 |
| Trp | Trp | Leu | Ile | Ala | Tyr | Gly | Arg | Gly | Asp | Leu | Glu | His | Leu | Glu | Asp | |
| | 80 | | | | | 85 | | | | | 90 | | | | | |
| ACC | GCG | TGG | ACC | CCG | TGC | GTC | AAC | AAC | CTC | AAC | GGC | TTC | GTG | GCC | GCC | 637 |
| Thr | Ala | Trp | Thr | Pro | Cys | Val | Asn | Asn | Leu | Asn | Gly | Phe | Val | Ala | Ala | |
| 95 | | | | 100 | | | | | 105 | | | | | 110 | | |
| TTC | CTC | TTC | TCC | ATC | GAG | ACG | GAG | ACC | ACC | ATC | GGC | TAT | GGG | CAC | CGC | 685 |
| Phe | Leu | Phe | Ser | Ile | Glu | Thr | Glu | Thr | Thr | Ile | Gly | Tyr | Gly | His | Arg | |
| | | | | 115 | | | | 120 | | | | | | 125 | | |
| GTC | ATC | ACC | GAC | CAG | TGT | CCC | GAG | GGC | ATC | GTG | CTG | CTG | CTG | CTG | CAG | 733 |
| Val | Ile | Thr | Asp | Gln | Cys | Pro | Glu | Gly | Ile | Val | Leu | Leu | Leu | Leu | Gln | |
| | | | 130 | | | | | 135 | | | | | 140 | | | |
| GCT | ATC | CTG | GGC | TCC | ATG | GTG | AAC | GCT | TTC | ATG | GTG | GGC | TGC | ATG | TTC | 781 |
| Ala | Ile | Leu | Gly | Ser | Met | Val | Asn | Ala | Phe | Met | Val | Gly | Cys | Met | Phe | |
| | | 145 | | | | | 150 | | | | | 155 | | | | |
| GTC | AAG | ATC | TCG | CAG | CCC | AAC | AAG | CGC | GCC | GCC | ACT | CTC | GTC | TTC | TCC | 829 |
| Val | Lys | Ile | Ser | Gln | Pro | Asn | Lys | Arg | Ala | Ala | Thr | Leu | Val | Phe | Ser | |
| | 160 | | | | | 165 | | | | | 170 | | | | | |
| TCG | CAC | GCC | GTG | GTG | TCT | CTG | CGC | GAC | GGG | CGC | CTC | TGT | CTC | ATG | TTT | 877 |
| Ser | His | Ala | Val | Val | Ser | Leu | Arg | Asp | Gly | Arg | Leu | Cys | Leu | Met | Phe | |
| 175 | | | | | 180 | | | | | 185 | | | | | 190 | |
| CGC | GTG | GGC | GAC | CTG | CGA | TCC | TCA | CAC | ATC | GTC | GAG | GCC | TCC | ATC | CGA | 925 |
| Arg | Val | Gly | Asp | Leu | Arg | Ser | Ser | His | Ile | Val | Glu | Ala | Ser | Ile | Arg | |
| | | | | 195 | | | | 200 | | | | | 205 | | | |
| GCC | AAG | CTC | ATC | CGC | TCC | CGT | CAG | ACG | CTC | GAG | GGC | GAG | TTC | ATC | CCT | 973 |
| Ala | Lys | Leu | Ile | Arg | Ser | Arg | Gln | Thr | Leu | Glu | Gly | Glu | Phe | Ile | Pro | |
| | | | 210 | | | | | 215 | | | | | 220 | | | |
| TTG | CAC | CAG | ACC | GAC | CTC | AGC | GTG | GGC | TTT | GAC | ACG | GGG | GAC | GAC | CGC | 1021 |
| Leu | His | Gln | Thr | Asp | Leu | Ser | Val | Gly | Phe | Asp | Thr | Gly | Asp | Asp | Arg | |
| | | 225 | | | | | 230 | | | | | 235 | | | | |
| CTC | TTT | CTC | GTC | TCA | CCT | CTC | GTC | ATC | AGC | CAC | GAA | ATC | GAT | GCC | GCC | 1069 |
| Leu | Phe | Leu | Val | Ser | Pro | Leu | Val | Ile | Ser | His | Glu | Ile | Asp | Ala | Ala | |
| | 240 | | | | | 245 | | | | | 250 | | | | | |
| AGC | CCC | TTC | TGG | GAG | GCA | TCG | CGC | CGC | GCC | CTC | GAG | AGG | GAC | GAC | TTC | 1117 |
| Ser | Pro | Phe | Trp | Glu | Ala | Ser | Arg | Arg | Ala | Leu | Glu | Arg | Asp | Asp | Phe | |
| 255 | | | | | 260 | | | | | 265 | | | | | 270 | |
| GAG | ATC | GTA | GTC | ATT | CTC | GAG | GGC | ATG | GTG | GAG | GCC | ACG | GGA | ATG | ACG | 1165 |
| Glu | Ile | Val | Val | Ile | Leu | Glu | Gly | Met | Val | Glu | Ala | Thr | Gly | Met | Thr | |
| | | | | 275 | | | | | 280 | | | | | 285 | | |
| TGC | CAA | GCT | CGA | AGC | TCG | TAC | CTG | GTG | GAT | GAA | GTG | TTG | TGG | GGA | CAC | 1213 |
| Cys | Gln | Ala | Arg | Ser | Ser | Tyr | Leu | Val | Asp | Glu | Val | Leu | Trp | Gly | His | |
| | | | 290 | | | | | 295 | | | | | 300 | | | |
| CGG | TTC | ACA | TCC | GTG | CTC | ACC | CTG | GAG | GAT | GGT | TTC | TAT | GAG | GTG | GAC | 1261 |
| Arg | Phe | Thr | Ser | Val | Leu | Thr | Leu | Glu | Asp | Gly | Phe | Tyr | Glu | Val | Asp | |
| | | 305 | | | | | 310 | | | | | 315 | | | | |
| TAC | GCC | AGC | TTC | CAC | GAA | ACC | TTT | GAG | GTG | CCC | ACA | CCC | TCG | TGC | AGT | 1309 |
| Tyr | Ala | Ser | Phe | His | Glu | Thr | Phe | Glu | Val | Pro | Thr | Pro | Ser | Cys | Ser | |
| | 320 | | | | | 325 | | | | | 330 | | | | | |
| GCT | CGG | GAA | CTG | GCA | GAA | GCC | GCG | GCC | CGC | CTT | GAT | GCC | CAT | CTC | TAC | 1357 |
| Ala | Arg | Glu | Leu | Ala | Glu | Ala | Ala | Ala | Arg | Leu | Asp | Ala | His | Leu | Tyr | |
| 335 | | | | 340 | | | | | 345 | | | | | 350 | | |
| TGG | TCC | ATC | CCC | AGC | AGG | CTG | GAT | GAG | AAG | GTG | GAG | GAA | GAA | GGG | GCT | 1405 |
| Trp | Ser | Ile | Pro | Ser | Arg | Leu | Asp | Glu | Lys | Val | Glu | Glu | Glu | Gly | Ala | |
| | | | | 355 | | | | | 360 | | | | | 365 | | |
| GGG | GAG | GGG | GGC | AGG | TGC | GGG | AGA | TGG | AGC | TGACAAGGAG | CACAATGGCT | | | | | 1455 |
| Gly | Glu | Gly | Gly | Arg | Cys | Gly | Arg | Trp | Ser | | | | | | | |
| | | | 370 | | | | | 375 | | | | | | | | |

GCCACCCCCA GAGAGTGAGT CCAAGGTGTG ACTGGTTTCC TCCCACCCCC TGTGGCAGAC 1515

CAGGGGGCCG GACTCAGGTA CACAGAAGCT GCGAGTGGAG GTGGAAGAAG AGGAGGCAGG 1575

```
CAGTGTCCCG AGGAACAGCT AAAGTTGGGA GAGGCCCGCT GAGTCCAGGA TCGAGTAGGG    1635

AAGGCTGAGG TCCTGGTTTG AAGAGAGAGG GTTGCAGGGC GGGGTGAGAG AACATGTCAG    1695

TCTGTCTGTG TTTGACCTTC ACATCGGTTC ATGGGTGGAT GGATGGACAG AAGGATGGGC    1755

TCATGGGGGT TGATCGGGAA GGTGGAGCAG ATAGAGACAG CCAATGGATA ATCGCTCAGG    1815

TGGTAAGTGG CTTGGCAGTC GATGATCGTC ACCTGCAGCA CACCTTTGTG AGAAATCCAT    1875

GGCATCCTT TTCTTCCAGA TATAGGTAGC CTCAAACCAG GGAGCGTGGC TTAGGGAGCA     1935

GGCTGTCAGG TGGACTACCA CCCCCACTCA CCTCCCCTCA ACTGGCCTCC CTGATGTGTG    1995

ACACGCCTGC CTAACTAGAG AAGAGAGCAC TGGGTAGAGG TGGACACAGG TGTGGCTGCC    2055

CTCCCCAGTA TCACTGTCCC ATGGCGAGAG GTCAGAAAGG CAAACAAACA ATGGGGGTAG    2115

ATGCTGAGCA GGGAGGGGCC CTGAAGCAGG ACCTGGGGAC AGCCAAGGAC AACTATTTTG    2175

TGAGAGAGGA ATGAAACCTT GCAGGTCCTG CCACAGAAGC AAGAAGCAGA GGAAAGGCCA    2235

TGGAGAGACT TAATAAAGGG TTTTACAAGG GAAAAAAAA AAAAAAAAAA AAAAAAAAA    2295

AAAAAA                                                              2301
```

( 2 ) INFORMATION FOR SEQ ID NO:6:

( i ) SEQUENCE CHARACTERISTICS:
        ( A ) LENGTH: 376 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Gln Glu Asn Ala Ala Phe Ser Pro Gly Ser Glu Glu Pro Pro
 1               5                  10                  15

Arg Arg Arg Gly Arg Gln Arg Tyr Val Glu Lys Asp Gly Arg Cys Asn
            20                  25                  30

Val Gln Gln Gly Asn Val Arg Glu Thr Tyr Arg Tyr Leu Thr Asp Leu
        35                  40                  45

Phe Thr Thr Leu Val Asp Leu Gln Trp Arg Leu Arg Leu Leu Phe Phe
    50                  55                  60

Val Leu Ala Tyr Ala Leu Thr Trp Leu Phe Phe Gly Val Ile Trp Trp
65                  70                  75                  80

Leu Ile Ala Tyr Gly Arg Gly Asp Leu Glu His Leu Glu Asp Thr Ala
                85                  90                  95

Trp Thr Pro Cys Val Asn Asn Leu Asn Gly Phe Val Ala Ala Phe Leu
            100                 105                 110

Phe Ser Ile Glu Thr Glu Thr Thr Ile Gly Tyr Gly His Arg Val Ile
        115                 120                 125

Thr Asp Gln Cys Pro Glu Gly Ile Val Leu Leu Leu Leu Gln Ala Ile
    130                 135                 140

Leu Gly Ser Met Val Asn Ala Phe Met Val Gly Cys Met Phe Val Lys
145                 150                 155                 160

Ile Ser Gln Pro Asn Lys Arg Ala Ala Thr Leu Val Phe Ser Ser His
                165                 170                 175

Ala Val Val Ser Leu Arg Asp Gly Arg Leu Cys Leu Met Phe Arg Val
            180                 185                 190

Gly Asp Leu Arg Ser Ser His Ile Val Glu Ala Ser Ile Arg Ala Lys
        195                 200                 205

Leu Ile Arg Ser Arg Gln Thr Leu Glu Gly Glu Phe Ile Pro Leu His
    210                 215                 220
```

| Gln 225 | Thr | Asp | Leu | Ser | Val 230 | Gly | Phe | Asp | Thr | Gly 235 | Asp | Asp | Arg | Leu | Phe 240 |
|---|---|---|---|---|---|---|---|---|---|---|---|---|---|---|---|
| Leu | Val | Ser | Pro | Leu 245 | Val | Ile | Ser | His | Glu 250 | Ile | Asp | Ala | Ala | Ser 255 | Pro |
| Phe | Trp | Glu | Ala 260 | Ser | Arg | Arg | Ala | Leu 265 | Glu | Arg | Asp | Asp | Phe 270 | Glu | Ile |
| Val | Val | Ile 275 | Leu | Glu | Gly | Met | Val 280 | Glu | Ala | Thr | Gly | Met 285 | Thr | Cys | Gln |
| Ala | Arg 290 | Ser | Ser | Tyr | Leu 295 | Val | Asp | Glu | Val | Leu | Trp 300 | Gly | His | Arg | Phe |
| Thr 305 | Ser | Val | Leu | Thr | Leu 310 | Glu | Asp | Gly | Phe | Tyr 315 | Glu | Val | Asp | Tyr | Ala 320 |
| Ser | Phe | His | Glu | Thr 325 | Phe | Glu | Val | Pro | Thr 330 | Pro | Ser | Cys | Ser | Ala 335 | Arg |
| Glu | Leu | Ala | Glu 340 | Ala | Ala | Ala | Arg | Leu 345 | Asp | Ala | His | Leu | Tyr 350 | Trp | Ser |
| Ile | Pro | Ser 355 | Arg | Leu | Asp | Glu | Lys 360 | Val | Glu | Glu | Glu | Gly 365 | Ala | Gly | Glu |
| Gly | Gly 370 | Arg | Cys | Gly | Arg | Trp 375 | Ser | | | | | | | | |